US009452131B2

(12) United States Patent
Hickey et al.

(10) Patent No.: US 9,452,131 B2
(45) Date of Patent: Sep. 27, 2016

(54) ARIPIPRAZOLE FORMULATIONS HAVING INCREASED INJECTION SPEEDS

(71) Applicant: ALKERMES PHARMA IRELAND LIMITED, Dublin (IE)

(72) Inventors: Magali B. Hickey, Westwood, MA (US); Jennifer Vandiver, Arlington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 14/663,042

(22) Filed: Mar. 19, 2015

(65) Prior Publication Data

US 2015/0265529 A1 Sep. 24, 2015

Related U.S. Application Data

(60) Provisional application No. 61/955,976, filed on Mar. 20, 2014.

(51) Int. Cl.
*A61K 31/497* (2006.01)
*A61K 9/00* (2006.01)
*A61K 31/496* (2006.01)
*A61K 47/26* (2006.01)

(52) U.S. Cl.
CPC ........... *A61K 9/0019* (2013.01); *A61K 31/496* (2013.01); *A61K 47/26* (2013.01)

(58) Field of Classification Search
CPC ........... Y10S 514/962; Y10S 514/963; Y10S 514/964; Y10S 514/965; Y10S 514/929; C07D 471/04; C07D 215/22; C07D 263/58; C07D 401/12; C07D 401/14; C07D 417/12; C07D 215/227; C07D 417/14; C07D 489/08
See application file for complete search history.

(56) References Cited

U.S. PATENT DOCUMENTS

| | | |
|---|---|---|
| 2,418,499 A | 4/1947 | Burke |
| 3,266,984 A | 8/1966 | Katsuji |
| 3,523,121 A | 8/1970 | Lewis et al. |
| 3,573,308 A | 3/1971 | Ning et al. |
| 3,957,808 A | 5/1976 | Miller et al. |
| 4,160,099 A | 7/1979 | Bodor |
| 4,204,065 A | 5/1980 | Bodor |
| 4,260,769 A | 4/1981 | Stella |
| 4,428,935 A | 1/1984 | Myers |
| 4,443,464 A | 4/1984 | Biedermann et al. |
| 4,594,190 A | 6/1986 | Giani et al. |
| 4,694,006 A | 9/1987 | Bundgaard et al. |
| 4,727,151 A | 2/1988 | Bodor |
| 4,760,057 A | 7/1988 | Alexander |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,236,927 A | 8/1993 | Jones et al. |
| 5,350,747 A | 9/1994 | Howard |
| 5,462,934 A | 10/1995 | Goto et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,945,416 A | 8/1999 | Shannon et al. |
| 5,985,856 A | 11/1999 | Stella et al. |
| 6,127,357 A | 10/2000 | Cliffe et al. |
| 6,133,248 A | 10/2000 | Stella |
| 6,180,095 B1 | 1/2001 | Greenwald et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 6,977,257 B2 | 12/2005 | Parab et al. |
| 7,053,092 B2 | 5/2006 | Jordon et al. |
| 7,112,603 B2 | 9/2006 | Moon et al. |
| 7,115,587 B2 | 10/2006 | Nerurkar |
| 7,160,888 B2 | 1/2007 | Johnson et al. |
| 7,538,121 B2 | 5/2009 | MacDonald et al. |
| 7,550,445 B2 | 6/2009 | Nerurkar et al. |
| 7,807,680 B2 | 10/2010 | Kostanski et al. |
| 7,910,577 B2 | 3/2011 | Liversidge et al. |
| 7,981,906 B2 | 7/2011 | Dull et al. |
| 8,017,515 B2 | 9/2011 | Marimuthu et al. |
| 8,030,313 B2 | 10/2011 | Kostanski et al. |
| 8,338,427 B2 | 12/2012 | Brown |
| 8,338,428 B2 | 12/2012 | Brown |
| 8,399,469 B2 | 3/2013 | Bando et al. |
| 8,431,576 B2 | 4/2013 | Remenar et al. |
| 8,518,421 B2 | 8/2013 | Kothari et al. |

(Continued)

FOREIGN PATENT DOCUMENTS

| | | |
|---|---|---|
| DE | 1273533 B | 7/1968 |
| EP | 0925061 B1 | 12/2005 |

(Continued)

OTHER PUBLICATIONS

Cocoman, Journal of Psychiatric and Mental Health Nursing, Jul. 2008.*
Medication Administration Techniques, Injections, copyright 1995-2010.*
International Search Report and Written Opinion for International Application No. PCT/US2013/060677, dated Jan. 10, 2014, 7 pages.
International Search Report and Written Opinion for International Application No. PCT/US2013/030945, dated Jun. 26, 2013, 17 pages.
International Search Report and Written Opinion for International Application No. PCT/US2013/030916, dated Aug. 26, 2013, 18 pages.
International Search Report and Written Opinion for International Application No. PCT/US2013/030933, dated Jun. 26, 2013, 14 pages.
International Search Report and Written Opinion for International Application No. PCT/IB2013/002995, dated Jun. 11, 2014, 10 pages.

(Continued)

*Primary Examiner* — Jean Cornet
(74) *Attorney, Agent, or Firm* — Lathrop & Gage LLP; Brian C. Trinque; Jana A. Lewis

(57) ABSTRACT

The present invention relates to pharmaceutical compositions comprising a compound of Formula (I) that are useful for the intramuscular delivery of antipsychotic drugs using rapid injection rates.

24 Claims, 6 Drawing Sheets

(56) References Cited

U.S. PATENT DOCUMENTS

| | | |
|---|---|---|
| 8,536,328 B2 | 9/2013 | Remenar et al. |
| 8,580,796 B2 | 11/2013 | Bando et al. |
| 8,642,600 B2 | 2/2014 | Jordan et al. |
| 8,642,760 B2 | 2/2014 | Bando et al. |
| 9,034,867 B2 | 5/2015 | Perry et al. |
| 2002/0176841 A1 | 11/2002 | Barker et al. |
| 2003/0064998 A1 | 4/2003 | Francois et al. |
| 2004/0101557 A1 | 5/2004 | Gibson et al. |
| 2005/0032811 A1 | 2/2005 | Brown et al. |
| 2005/0203089 A1 | 9/2005 | Starrett, Jr. et al. |
| 2005/0282821 A1 | 12/2005 | Lesur et al. |
| 2006/0040922 A1 | 2/2006 | Greco et al. |
| 2006/0142333 A1 | 6/2006 | MacDonald et al. |
| 2006/0154918 A1 | 7/2006 | Liversidge et al. |
| 2006/0194345 A1 | 8/2006 | Uchiyama et al. |
| 2006/0293217 A1 | 12/2006 | Barker et al. |
| 2007/0031513 A1 | 2/2007 | Kikuchi et al. |
| 2007/0191611 A1 | 8/2007 | Rao et al. |
| 2008/0085888 A1 | 4/2008 | Breining et al. |
| 2008/0186971 A1 | 8/2008 | Carmichael et al. |
| 2008/0233053 A1 | 9/2008 | Gross et al. |
| 2008/0261954 A1 | 10/2008 | Maelicke |
| 2008/0312199 A1 | 12/2008 | Glinsky |
| 2008/0318905 A1 | 12/2008 | Muhammad et al. |
| 2009/0053329 A1 | 2/2009 | Peters et al. |
| 2009/0068290 A1 | 3/2009 | Bourin et al. |
| 2009/0118242 A1 | 5/2009 | Burch et al. |
| 2009/0143403 A1 | 6/2009 | Brown |
| 2009/0163519 A1 | 6/2009 | Vermeulen et al. |
| 2009/0163545 A1 | 6/2009 | Goldfarb |
| 2009/0169632 A1 | 7/2009 | Lu et al. |
| 2009/0311347 A1 | 12/2009 | Oronsky et al. |
| 2010/0197641 A1 | 8/2010 | Mazess et al. |
| 2010/0286136 A1 | 11/2010 | Jones et al. |
| 2010/0292316 A1 | 11/2010 | Sanders et al. |
| 2011/0003828 A1 | 1/2011 | Blumberg |
| 2011/0015156 A1 | 1/2011 | Remenar et al. |
| 2011/0166128 A1 | 7/2011 | Remenar et al. |
| 2011/0166156 A1 | 7/2011 | Blumberg et al. |
| 2011/0166194 A1 | 7/2011 | Blumberg et al. |
| 2011/0178068 A1 | 7/2011 | Almarsson et al. |
| 2011/0195095 A1 | 8/2011 | Liversidge et al. |
| 2011/0236478 A1 | 9/2011 | Dokou et al. |
| 2011/0275803 A1 | 11/2011 | Remenar et al. |
| 2011/0319422 A1 | 12/2011 | Blumberg et al. |
| 2012/0015866 A1 | 1/2012 | Blumberg et al. |
| 2012/0238552 A1 | 9/2012 | Perry et al. |
| 2013/0096089 A1 | 4/2013 | Remenar et al. |
| 2013/0267503 A1 | 10/2013 | Perry et al. |
| 2013/0267504 A1 | 10/2013 | Perry et al. |
| 2013/0267505 A1 | 10/2013 | Perry et al. |
| 2014/0088115 A1 | 3/2014 | Perry et al. |

FOREIGN PATENT DOCUMENTS

| | | |
|---|---|---|
| EP | 1891956 A1 | 2/2008 |
| GB | 849541 A1 | 9/1960 |
| GB | 2017701 A | 10/1979 |
| WO | 9014080 A1 | 11/1990 |
| WO | 9100863 A1 | 1/1991 |
| WO | 9325197 A1 | 12/1993 |
| WO | 9612725 A1 | 5/1996 |
| WO | 9743284 A1 | 11/1997 |
| WO | 9933846 A2 | 7/1999 |
| WO | 0249573 | 6/2002 |
| WO | 02096351 A2 | 12/2002 |
| WO | 2004026864 A1 | 4/2004 |
| WO | 2004067546 A1 | 8/2004 |
| WO | 2004089925 A1 | 10/2004 |
| WO | 2005066165 A1 | 7/2005 |
| WO | 2005079807 A1 | 9/2005 |
| WO | 2006037090 A1 | 4/2006 |
| WO | 2006055603 | 5/2006 |
| WO | 2006090273 A2 | 8/2006 |
| WO | 2007018943 A2 | 2/2007 |
| WO | 2007059111 A2 | 5/2007 |
| WO | 2008124030 A1 | 10/2008 |
| WO | 2009052467 A1 | 4/2009 |
| WO | 2009060473 A2 | 5/2009 |
| WO | 2010135703 | 11/2010 |
| WO | 2010151689 | 12/2010 |
| WO | 2010151711 A1 | 12/2010 |
| WO | 2011084846 A1 | 7/2011 |
| WO | 2011084848 A2 | 7/2011 |
| WO | 2012129156 | 9/2012 |

OTHER PUBLICATIONS

International Search Report and Written Opinion for International Application No. PCT/US2012/029625, dated Jun. 15, 2012, 18 pages.

U.S. Appl. No. 14/688,050, filed Apr. 16, 2015, Jason M. Perry et al.

U.S. Appl. No. 14/714,621, filed May 18, 2015, Jason M. Perry et al.

Partial File History of U.S. Appl. No. 13/423,606, filed Mar. 19, 2012, 62 pages.

Shintani, et al: A new method to determine the irritation of drugs after intramuscular injection in rabbits; Toxicology and Applied Pharmacology; Academic Press, U.S., Sep. 1, 1967; Vo. 11, No. 2, pp. 293-295.

\* cited by examiner

ARIPIPRAZOLE FORMULATIONS HAVING INCREASED INJECTION SPEEDS

RELATED APPLICATIONS

This application claims priority to U.S. Provisional Application Ser. No. 61/955,976 filed on Mar. 20, 2014, the contents of which is hereby incorporated by reference in its entirety.

BACKGROUND

U.S. Pat. Nos. 4,734,416 and 5,006,528 disclose aripiprazole, 7-{4-[4-(2,3-dichlorophenyl)-1-piperazinyl]butoxy}-3,4-dihydro-2(1H)-quinolinone or 7-{4-[4-(2,3-dichlorophenyl)-1-piperazinyl]butoxy}-3,4-dihydro carbostyril, as an atypical antipsychotic agent useful in the treatment of schizophrenia, bipolar disease, depression, and other CNS disorders. Aripiprazole has the following chemical structure:

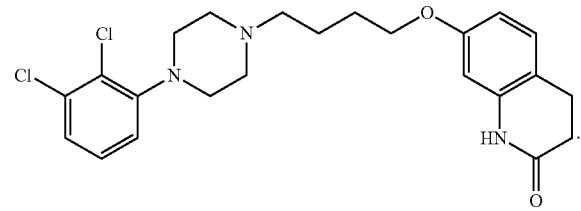 [SMILES: O=C1CCc2ccc(OCCCCN3CCN(c4cccc(Cl)c4Cl)CC3)cc2N1]

Aripiprazole is sold under the trade name ABILIFY®. It acts as a dopamine $D_2$ partial agonist, serotonin $5\text{-}HT_{1A}$ receptor agonist, and is an antagonist of the serotonin $5\text{-}HT_{2A}$ receptor. ABILIFY® is currently administered orally on a once-a-day dosing schedule as ABILIFY® (aripiprazole) Tablets, ABILIFY DISCMELT® (aripiprazole) Orally Disintegrating Tablets, and ABILIFY® (aripiprazole) Oral Solution. Poor and variable patient compliance with a once-a-day dosing schedule of psychiatric drugs has been reported. Efforts have been made to provide drug dosage forms that may increase the compliance of patients and thereby lower the rate of relapse in the treatment of schizophrenia.

U.S. Pat. Nos. 7,807,680, 8,338,427, and 8,338,428 describe long-acting aripiprazole sterile injectable formulations. Studies on aripiprazole free base injections showed a prolonged pharmacokinetic profile, but there have been reports of moderate to severe tissue irritation following intramuscular (IM) injection and subcutaneous (SC) injection. As such, there exists a need for improved methods of delivering antipsychotics, such as aripiprazole, thereby improving patient compliance and maximizing the pharmacological profile of the active agent.

SUMMARY OF THE INVENTION

In part, the invention provided herein relates to the intramuscular administration of pharmaceutical compositions comprising compounds of Formula (I) to a subject in need thereof using a rapid injection rate. It was discovered that the rapid injection rate resulted in fewer injection site failures, such as needle clogging. Surprisingly, the rapid injection rate did not cause a pain intensity above a normal threshold or any injection site reactions in the subject in need thereof. Thus, provided herein is an improved method of administering pharmaceutical compositions comprising compounds of Formula (I), wherein the method comprises intramuscular administration using a rapid or instantaneous injection speed.

In one aspect, provided herein are methods of using pharmaceutical compositions comprising compounds of Formula (I) to treat disorders of the central nervous system, such as schizophrenia. In another aspect, provided herein is a method of intramuscular administration of a pharmaceutical composition to a subject in need thereof, comprising administering to said subject a therapeutically effective amount of the composition at an injection rate greater than or equal to 0.3 mL/s, wherein said pharmaceutical composition comprises:

(a) 24-30 weight percent of a compound of Formula (I):

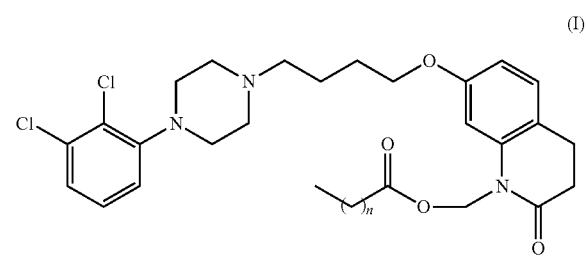

wherein n is an integer between 4 and 14;
(b) 0.3-0.4 weight percent sorbitan laurate;
(c) 0.1-0.3 weight percent polysorbate 20; and
(d) an aqueous vehicle wherein the percentages of (a), (b), and (c) are relative to the total weight of the composition.

In another embodiment, the pharmaceutical composition comprises:

(a) about 26.6 weight percent of a compound of Formula (I);
(b) about 0.37 weight percent sorbitan laurate;
(c) about 0.15 weight percent polysorbate 20; and
(d) an aqueous vehicle wherein the percentages of (a), (b), and (c) are relative to the total weight of the composition.

In another embodiment, component (a) of the pharmaceutical composition comprises a compound of Formula (I):

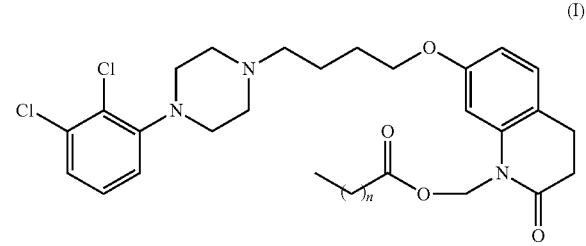

wherein n is an integer between 9 and 11.

In yet another embodiment, the pharmaceutical composition comprises:

(a) 24-30 weight percent Compound 1:

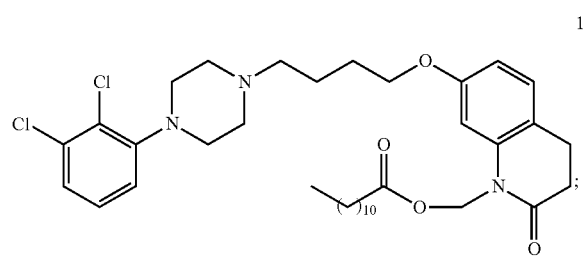

(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition.

In still another embodiment, the said pharmaceutical composition comprises:
(a) about 26.6 weight percent Compound 1;
(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

In some embodiments of the method, the injection is administered to the subject in the dorsal gluteal muscle. In other embodiments of the method, the injection is administered to the subject in the deltoid muscle.

In some embodiments of the method, the needle does not experience injection failure due to needle clogging.

In other embodiments, the method does not elicit a pain intensity above a normal threshold in the subject. In other embodiments, the method does not elicit any injection site reactions in the subject.

In another aspect, provided herein is a method of treating a disorder of the central nervous system in a subject in need thereof, comprising administering to said subject a therapeutically effective amount of the composition at an intravenous injection rate greater than or equal to 0.3 mL/s. In one embodiment of the method, the disorder is schizophrenia.

In certain embodiments of the methods described above, the intramuscular injection rate is greater than 0.3 mL/s.

In another aspect, provided herein is a kit useful for the treatment of a disorder of the central nervous system, comprising a therapeutically effective amount of a pharmaceutical composition and further comprising instructions for intramuscular injection, wherein the intramuscular injection rate is greater than or equal to 0.3 mL/s. In one embodiment, the kit is adapted to be associated with a treatment regimen. In another embodiment of the kit, the intramuscular injection rate is greater than 0.3 mL/s.

DETAILED DESCRIPTION

Figure 1:
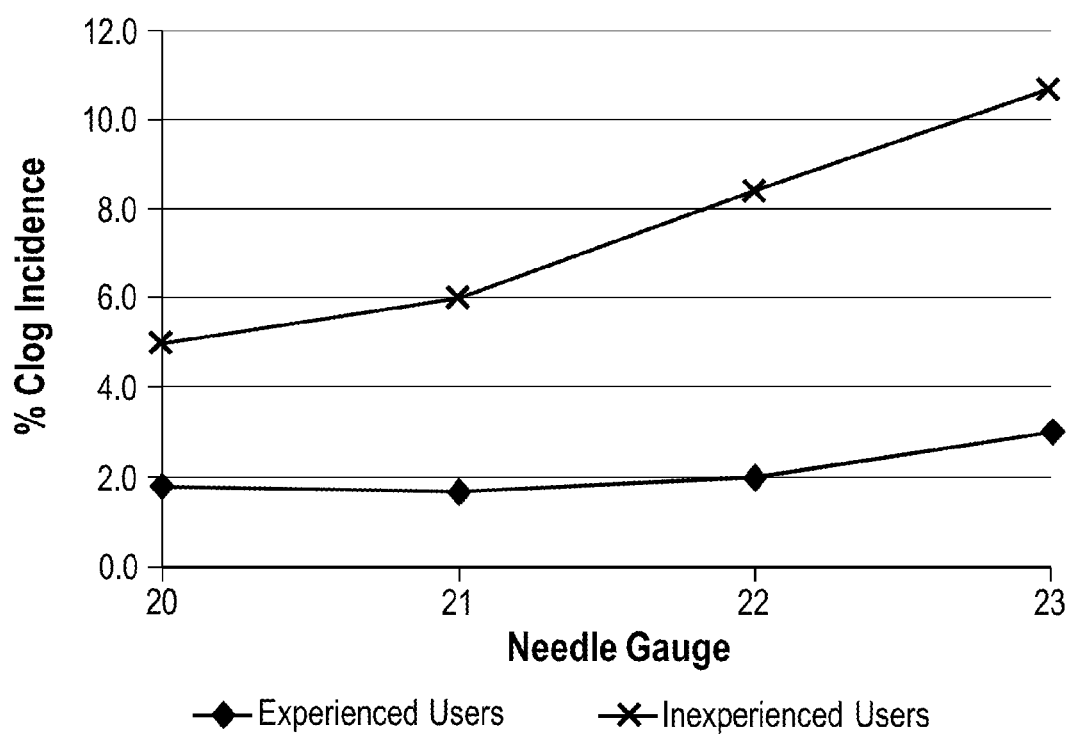
FIG. 1 shows the occurrence of needle clogs as a function of needle gauge and user experience upon injection of a pharmaceutical composition comprising Compound 1 into an open cell polyurethane foam substrate.

In part, the invention provided herein relates to the intramuscular administration of pharmaceutical compositions comprising compounds of Formula (I) to a subject in need thereof using a rapid injection rate. It was discovered that the rapid injection rate resulted in fewer injection site failures, such as needle clogging. Surprisingly, the rapid injection rate did not cause a pain intensity above a normal threshold or any injection site reactions in the subject in need thereof. Thus, provided herein is an improved method of administering pharmaceutical compositions comprising compounds of Formula (I), wherein the method comprises intramuscular administration using a rapid or instantaneous injection speed.

Pharmaceutical Compositions and Methods of Administering

Provided herein is an improved method of administering pharmaceutical compositions comprising a compound of Formula (I):

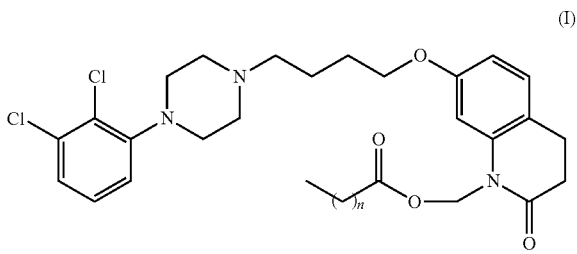

wherein n is an integer between 4 and 14;
wherein the method comprises intramuscular administration using a rapid or instantaneous injection speed.

In another embodiment, the pharmaceutical composition comprises a compound of Formula (I):

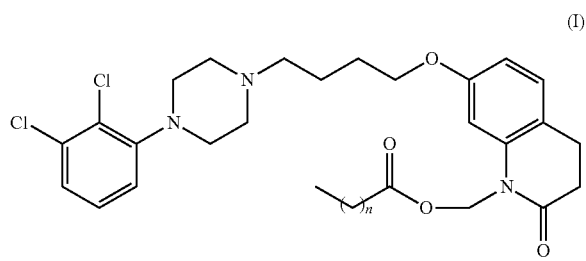

wherein n is an integer between 9 and 11.

In one aspect, provided herein is a method of intramuscular administration of a pharmaceutical composition to a subject in need thereof, comprising administering to said subject a therapeutically effective amount of the composition at an injection rate greater than or equal to 0.3 mL/s, wherein said pharmaceutical composition comprises:
(a) a compound of Formula (I):

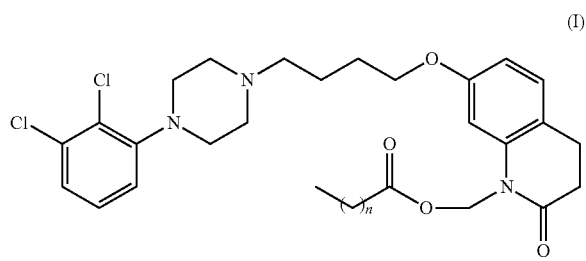

wherein n is an integer between 4 and 14;

(b) sorbitan laurate;
(c) polysorbate 20; and
(d) an aqueous vehicle.

In one embodiment, the pharmaceutical composition comprises:
(a) a compound of Formula (I):

*[Chemical structure of Formula (I)]* wherein n is an integer between 9 and 11;
(b) sorbitan laurate;
(c) polysorbate 20; and
(d) an aqueous vehicle.

Also provided herein are methods of administering pharmaceutical compositions, wherein the pharmaceutical compositions comprise approximately 15-35 weight percent of a compound of Formula (I). In one embodiment of the method, the composition comprises approximately 20-30 weight percent of a compound of Formula (I). In another embodiment of the method, the composition comprises approximately 24-30 weight percent of a compound of Formula (I). In a particular embodiment of the method, the composition comprises approximately 26.6 weight percent of a compound of Formula (I).

In an embodiment of the method, the pharmaceutical composition comprises:
(a) 15-35 weight percent of a compound of Formula (I):

*[Chemical structure of Formula (I)]* wherein n is an integer between 4 and 14;
(b) 0.25-0.45 weight percent sorbitan laurate;
(c) 0.2-1 weight percent polysorbate 20; and
(d) an aqueous vehicle
wherein the percentages of (a), (b), and (c) are relative to the total weight of the composition.

In another embodiment of the method, the pharmaceutical composition comprises:
(a) 15-35 weight percent of a compound of Formula (I):

*[Chemical structure of Formula (I)]* wherein n is an integer between 9 and 11;
(b) 0.25-0.45 weight percent sorbitan laurate;
(c) 0.2-1 weight percent polysorbate 20; and
(d) an aqueous vehicle
wherein the percentages of (a), (b), and (c) are relative to the total weight of the composition.

In yet another embodiment of the method, the pharmaceutical composition comprises:
(a) 24-30 weight percent of a compound of Formula (I):

*[Chemical structure of Formula (I)]* wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition.

In still another embodiment of the method, the pharmaceutical composition comprises:
(a) 24-30 weight percent of a compound of Formula (I):

*[Chemical structure of Formula (I)]* wherein n is an integer between 9 and 11;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition.

In one embodiment of the method, the pharmaceutical composition comprises:
(a) about 26.6 weight percent of a compound of Formula (I):

*[Chemical structure of Formula (I)]* wherein n is an integer between 4 and 14;

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

In another embodiment of the method, the pharmaceutical composition comprises:
(a) about 26.6 weight percent of a compound of Formula (I):

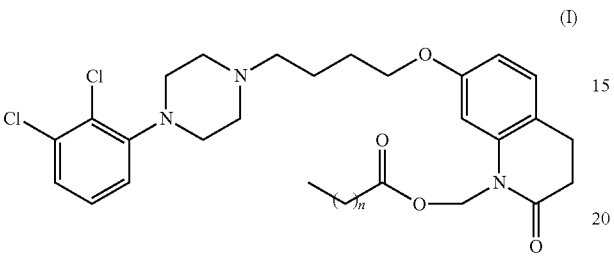

(I)

wherein n is an integer between 9 and 11;
(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

In yet another embodiment of the method, the pharmaceutical composition comprises:
(a) 15-35 weight percent Compound 1:

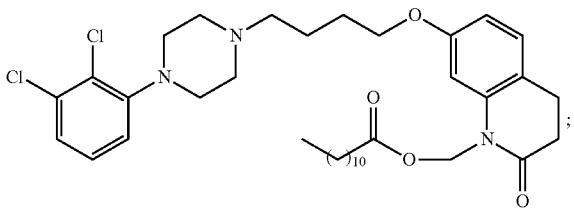

1

(b) 0.25-0.45 weight percent sorbitan laurate;
(c) 0.2-1 weight percent polysorbate 20; and
(d) an aqueous vehicle
wherein the percentages of (a), (b), and (c) are relative to the total weight of the composition.

In still another embodiment of the method, the pharmaceutical composition comprises:
(a) 24-30 weight percent Compound 1:

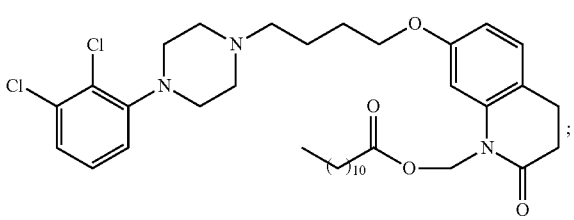

1

(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition.

In one embodiment of the method, the pharmaceutical composition comprises:
(a) about 26.6 weight percent Compound 1:

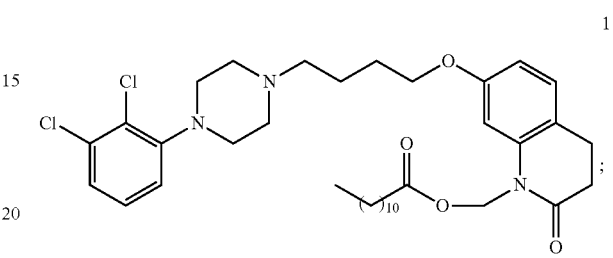

1

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

In another embodiment of the method, the pharmaceutical composition is injected at an injection rate greater than or equal to 0.3 mL/s.

Component (c), i.e., polysorbate 20, is sold under the trademark TWEEN®. The polysorbate can be added in an amount that reduces surface tension of a drug product or aids in suspension stability of the drug product.

The ratio of components (b) to (c) can vary. In one embodiment, the ratio of components (b) to (c) is approximately 10 to 0.5, e.g., 10 to 1, e.g., 8 to 1, e.g., 5 to 2, by weight. In another embodiment, the ratio of components (b) to (c) is approximately 5 to 2, by weight. In still another embodiment, the composition comprises sorbitan monolaurate (SML) or sorbitan laurate, and polysorbate 20, wherein the ratio of sorbitan laurate and polysorbate 20 is approximately 5 to 2, by weight. In still another embodiment, the composition comprises sorbitan laurate, and polysorbate 20, wherein the ratio of sorbitan laurate and polysorbate 20 is approximately 3 to 1, by weight. In another embodiment, the composition comprises sorbitan laurate, and polysorbate 20, wherein the ratio of sorbitan laurate and polysorbate 20 is approximately 2 to 1, by weight. In yet another embodiment, the composition comprises sorbitan laurate, and polysorbate 20, wherein the ratio of sorbitan laurate and polysorbate 20 is within the range of approximately 3 to 1-2 to 1, by weight. In a particular embodiment, the composition comprises sorbitan laurate, and polysorbate 20, wherein the ratio of sorbitan laurate and polysorbate 20 is approximately a ratio of 3 to a range of 1-2, by weight. In one embodiment, the composition comprises sorbitan laurate and polysorbate 20, wherein the ratio of sorbitan laurate and polysorbate 20 is approximately 3 to 1.2, by weight.

As described in Table 1 below, the sorbitan laurate/polysorbate 20 ratio can be approximately 0.625, 1, 1.25, 2, 2.5, or 5, representing a range of 0.625-5.

TABLE 1

Exemplary ratios of sorbitan monolaurate (SML) to
polysorbate 20 in example compositions of the invention.

| SML % | Polysorbate 20% | SML/Polysorbate 20 Ratio |
|---|---|---|
| 1 | 0.8 | 1.25 |
| 0.5 | 0.5 | 1 |
| 0.5 | 0.2 | 2.5 |
| 1 | 0.5 | 2 |
| 0.5 | 0.8 | 0.625 |
| 1 | 0.2 | 5 |
| 0.5 | 0.1 | 5 |

The weight percent of components (b) and (c) can vary in the pharmaceutical compositions provided herein. In one embodiment, the composition comprises about 0.2-1 weight percent sorbitan laurate. In another embodiment, the composition comprises about 0.4-0.7 weight percent sorbitan laurate. In still another embodiment, the composition comprises about 0.5 weight percent sorbitan laurate.

In another embodiment, the composition comprises about 0.25-0.45 weight percent sorbitan laurate. In another embodiment, the composition comprises about 0.3-0.4 weight percent sorbitan laurate. In still another embodiment, the composition comprises about 0.37 weight percent sorbitan laurate.

In another embodiment, the composition comprises about 0.05-0.8 weight percent polysorbate 20. In yet another embodiment, the composition comprises about 0.1-0.3 weight percent polysorbate 20. In still another embodiment, the composition comprises about 0.2 weight percent polysorbate 20. In yet another embodiment, the composition comprises about 0.15 weight percent polysorbate 20.

The compositions provided herein can also have varying amounts of a compound of Formula (I). In one embodiment, the composition comprises approximately 15-35 weight percent of a compound of Formula (I). In another embodiment, the composition comprises approximately 24-30 weight percent of a compound of Formula (I). In still another embodiment, the composition comprises approximately 20-26 weight percent of a compound of Formula (I). In a particular embodiment, the composition comprises approximately 26.6 weight percent of a compound of Formula (I).

The ratio of components (a) to (b) can vary. In one embodiment, the ratio of components (a) to (b) is within a range of 30 to 0.1-0.5, by weight. In another embodiment, the composition comprises a compound of Formula (I) and sorbitan laurate, wherein the ratio of the compound of Formula (I) to sorbitan laurate is within a range of 30 to 0.1-0.5, by weight. In yet another embodiment, the composition comprises Compound 1 and sorbitan laurate, wherein the ratio of Compound 1 to sorbitan laurate is within a range of 30 to 0.1-0.5, by weight.

In one embodiment, the ratio of components (a) to (b) is within a range of 30 to 0.3-0.5, by weight. In another embodiment, the composition comprises a compound of Formula (I) and sorbitan laurate, wherein the ratio of the compound of Formula (I) to sorbitan laurate is within a range of 30 to 0.3-0.5, by weight. In yet another embodiment, the composition comprises Compound 1 and sorbitan laurate, wherein the ratio of Compound 1 to sorbitan laurate is within a range of 30 to 0.3-0.5, by weight.

In one embodiment, the ratio of components (a) to (b) is approximately 30 to 0.5, by weight. In another embodiment, the composition comprises a compound of Formula (I) and sorbitan laurate, wherein the ratio of the compound of Formula (I) to sorbitan laurate is approximately 30 to 0.5, by weight. In yet another embodiment, the composition comprises Compound 1 and sorbitan laurate, wherein the ratio of Compound 1 to sorbitan laurate is approximately 30 to 0.5, by weight.

In ratio of components (a) to (c) also can vary. In one embodiment, the ratio of components (a) to (c) is within a range of 30 to 0.1-2, by weight. In another embodiment, the composition comprises a compound of Formula (I) and polysorbate 20, wherein the ratio of the compound of Formula (I) to polysorbate 20 is within a range of 30 to 0.1-2, by weight. In yet another embodiment, the composition comprises Compound 1 and polysorbate 20, wherein the ratio of Compound 1 to sorbitan laurate is within a range of 30 to 0.1-2, by weight.

In one embodiment, the ratio of components (a) to (c) is within a range of 30 to 0.1-0.4, by weight. In another embodiment, the composition comprises a compound of Formula (I) and polysorbate 20, wherein the ratio of the compound of Formula (I) to polysorbate 20 is within a range of 30 to 0.1-0.4, by weight. In yet another embodiment, the composition comprises Compound 1 and polysorbate 20, wherein the ratio of Compound 1 to sorbitan laurate is within a range of 30 to 0.1-0.4, by weight.

In one embodiment, the ratio of components (a) to (c) is approximately 30 to 0.2, by weight. In another embodiment, the composition comprises a compound of Formula (I) and sorbitan laurate, wherein the ratio of the compound of Formula (I) to sorbitan laurate is approximately 30 to 0.2, by weight. In yet another embodiment, the composition comprises Compound 1 and sorbitan laurate, wherein the ratio of Compound 1 to sorbitan laurate is approximately 30 to 0.2, by weight.

The aqueous vehicle of the pharmaceutical compositions provided herein can be a buffer. The buffer may be selected from a phosphate, citrate, tartrate, or acetate buffer. In a particular embodiment, the buffer is a phosphate buffer.

The pharmaceutical compositions provided herein can further comprise additional components. For example, the pharmaceutical compositions can also contain an aqueous vehicle, which is a vehicle that dilutes and suspends the drug. The vehicle of interest herein is one that is pharmaceutically acceptable (safe and non-toxic for administration to a human) and is useful for the preparation of a reconstituted formulation. Exemplary vehicles include sterile water, sterile water for injection (WFI), bacteriostatic water for injection (BWFI), a pH buffered solution (e.g., phosphate-buffered saline), sterile saline solution, Ringer's solution, or dextrose solution. The buffer can be phosphate, citrate, tartrate, or acetate. In a particular embodiment, the vehicle is phosphate-buffered saline, which is a water-based salt solution containing either sodium chloride or potassium chloride and either sodium phosphate or potassium phosphate. In one embodiment, the phosphate buffer comprises isotonic saline with 5-50 mM phosphate buffer at pH 4.0-9.0, e.g., 5.0-8.0, e.g., 5.0-7.5.

Optionally, the pharmaceutical compositions can further comprise a dispersant, such as, for example, carboxymethyl cellulose (CMC), carboxymethyl cellulose sodium, cross-linked sodium carboxymethyl cellulose, calcium carboxymethyl cellulose, and low substituted hydroxypropyl cellulose magnesium aluminum silicate, or a mixture thereof. In a particular embodiment, the pharmaceutical composition comprises carboxymethyl cellulose (CMC).

In one embodiment, the pharmaceutical composition comprises:
(a) a compound of Formula (I):

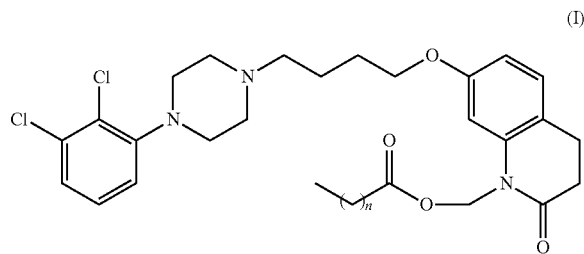

wherein n is an integer between 4 and 14;
(b) sorbitan laurate;
(c) polysorbate 20;
(d) CMC;
(e) sodium phosphate dibasic anhydrous;
(f) sodium dihydrogen phosphate monobasic dihydrate; and
(g) water for injection.

In another embodiment, the pharmaceutical composition comprises:
(a) a compound of Formula (I):

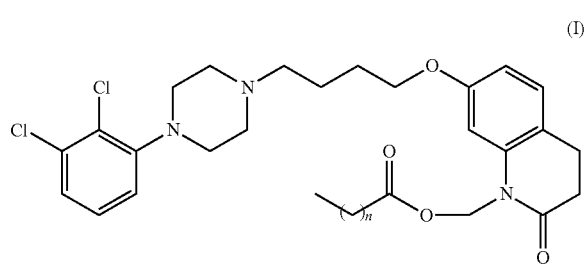

wherein n is an integer between 9 and 11;
(b) sorbitan laurate;
(c) polysorbate 20;
(d) CMC;
(e) sodium phosphate dibasic anhydrous;
(f) sodium dihydrogen phosphate monobasic dihydrate; and
(g) water for injection.

In yet another embodiment, the pharmaceutical composition comprises:
(a) Compound 1:

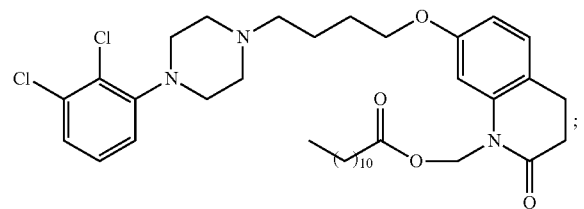

(b) sorbitan laurate;
(c) polysorbate 20;
(d) CMC;
(e) sodium phosphate dibasic anhydrous;
(f) sodium dihydrogen phosphate monobasic dihydrate; and
(g) water for injection.

The pharmaceutical compositions of these methods also offer minimized excipient levels while co-optimizing both re-suspendability and acceptable injectability, and maintain good physiochemical attributes of the antipsychotic agent. The compositions require reduced resuspension times using, for example, hand shaking. In one embodiment, the pharmaceutical compositions can be re-suspended for injection within 1-60 seconds of handshaking. Accordingly, the pharmaceutical compositions described herein can also be referred to as "ready to use."

When the pharmaceutical composition is to be used as an injectable composition, including but not limited to injection through a needle or needle-less injection, it can be formulated into a conventional injectable vehicle. Suitable vehicles include biocompatible and pharmaceutically acceptable solution and/or emulsions.

When the pharmaceutical composition is to be used as an injectable composition, including but not limited to injection through a needle or needle-less injection, it can be formulated into a conventional injectable vehicle. Suitable vehicles include biocompatible and pharmaceutically acceptable solution and/or emulsions.

The compositions provided herein do not elicit any injection site reactions normally associated with antipsychotic agents, such as aripiprazole, derivatives thereof, prodrugs thereof, and salts thereof.

As used herein, the term "injection site reaction" refers to inflammation or abnormal redness of the tissue and/or the skin at a site of injection in an individual.

The modulation of the tissue response following intramusclar (IM) administration is described by the spreadability of the drug and resulting depot morphology; spreading of the drug along the fascial planes of muscle is desirable rather than the formation of a concentrated mass of drug in a small area.

Depot morphology resulting from IM injection of aripiprazole and compounds of Formula (I) have been described. Injections of slow-releasing formulations of drugs, including aripiprazole commonly result in the formation of "cyst-like structures", characterized by a vascularized capsule of roughly spherical shape and comprising various cell types, with or without and a central serous fluid compartment. Tissue responses to slow-releasing formulations occur as the body mounts an immune response to clear the material from the injection site; this reaction is commonly referred to as a foreign body response (FBR). The spherical nature of these reactions can result in localized discomfort and pain, as the FBR increases in size compressing on nerve fibers innervating muscle tissue and with the release of pro-inflammatory cytokines from the site.

Surprisingly, the pharmaceutical compositions provided herein do not elicit an injection site reaction following IM administration. Therefore, in one embodiment, IM administration of the pharmaceutical compositions provided herein are associated with a reduced tissue and skin reaction at the site of injection. In one embodiment, the injection site reaction is reduced by a particular amount, e.g., about 90%, 80%, 70%, 60%, 50%, 40%, 30%, 20%, 10%, 5%, etc. In another embodiment, there is no injection site reaction following IM administration. In particular embodiments, there is no tissue or skin reaction at the site of injection following IM administration. In particular embodiments, IM administration is not associated with the symptoms of the injection site reaction, including, but not limited to: redness, tenderness, warmth, itching, pain at injection site, blistering, nodule formation, and severe skin damage. In one embodiment, components (a), (b), and (c) of the pharmaceutical composition are in a container, and the aqueous vehicle is in a separate container, wherein said container is any receptacle and closure therefor suitable for storing, shipping, dispensing, and/or handling a pharmaceutical product. Examples of such containers include, at least, for example, plastic and glass vials, ampules, pre-filled syringes and cartridges, and the like.

In certain embodiments, the pharmaceutical composition is stored in a sealed (e.g., septum stoppered), colorless, glass vial.

In other embodiments, pre-filled dual-chamber syringes and/or cartridges are utilized with the pharmaceutical compositions provided herein. Pre-filled dual-chamber syringes enable the sequential administration of two separate compositions with a single syringe push, thereby replacing two syringes with one. The benefits of a single delivery capability include increasing the speed and ease of drug administration; reducing risk of infection by reducing the number of connections; lowering the risk of drug administration or sequence errors, and quicker delivery of compositions requiring combination prior to administration. The dual-chamber syringe can accommodate lyophilized, powder, or liquid formulations in the front chamber combined with the aqueous vehicle.

Prefilled syringes can contain the exact deliverable dose of desired the pharmaceutical compositions provided herein. The prefilled syringes can contain volumes from about 0.1 mL, 0.2 mL, 0.3 mL, 0.4 mL, 0.5 mL, 0.6 mL, 0.7 mL, 0.8 mL, 0.9 mL, 1.0 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL or more or any other volume increment thereof.

The dual syringe and/or cartridge can be side-by-side chambers with separate syringe plungers that mix into a single chamber or linear chambers with one plunger. The dual chamber syringe and/or cartridges can also have a stopper or connector in the middle to serve as a barrier between the two chambers. The stopper or connector can be removed to allow mixing or combining of the individual components in the two chambers. For example, the front chamber can accommodate components (a), (b), and (c) of the pharmaceutical compositions provided herein, and the rear chamber can accommodate the aqueous vehicle. Thus, in one embodiment, the pre-filled dual-chamber syringe contains components (a), (b), and (c) of the pharmaceutical compositions provided herein in the front chamber and the aqueous vehicle in the rear chamber.

The pharmaceutical compositions can be formulated. The terms "pharmaceutical composition", "formulation", "injectable composition", etc. are used synonymously throughout the application.

The pharmaceutical compositions described herein may also be in the form of an emulsion. The term "emulsion" as used in this specification denotes a two-phase system in which one phase is finely dispersed in the other phase. An emulsifier can be used in the pharmaceutical compositions to form the emulsion. The term emulsifier, as used by this invention, denotes an agent that can reduce and/or eliminate the surface and the interfacial tension in a two-phase system. Such an agent possesses both hydrophilic and lipophilic groups in the emulsifier agent.

The pharmaceutical compositions described herein may also be in the form of a dispersion. As used herein, the term "dispersion" is to be understood as a mixture in which fine particles of one substance (e.g., a drug) are scattered throughout another substance (e.g., a liquid). Dispersions include suspensions and colloids.

The methods of the invention include administering the compositions described herein, thereby obtaining an extended release or sustained release profile in the patient. "Extended-release" or "sustained-release" includes dosage forms whose drug-release characteristics of time course and/or location are chosen to accomplish therapeutic or convenience objectives not offered by conventional dosage forms such as a solution or an immediate release dosage form. An extended release profile includes deliveries that achieve a therapeutically effective amount of compound of Formula (I) is present in the plasma of the individual for at least about 7 days, preferably at least about 14 days, or more preferably at least about 21 days; alternatively, for at least 2, 3, 4, 6, or 8 weeks, or as much as three months.

In one embodiment, the pharmaceutical compositions can be administered as a single or sole (undivided) dose. However, the composition is also useful for those individuals that require constant or chronic therapy, such as those that receive repeated doses over several hours, days, weeks, months, or more. In such dosing regimens, the method can comprise a first administration of a first extended release composition and a second administration of a second extended release composition. The second composition can be the same, substantially the same or different as the first and can include the same active agent or a different active agent. For example, the second composition can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The injectable, pharmaceutical compositions described herein can be injected into a patient in any number of ways. The term "injectable" as used herein refers to a composition that is suitable to be delivered to an individual in an injection, such as with an injection device, including one that employs a syringe or a cartridge, which may be housed in a manual injection device or an auto-injection device, for example. Specifically, the injectable composition is suitable for parenteral administration. As used herein, the term "parenteral administration" refers to administration through injection or infusion. Parenteral administration includes, but is not limited to, intravenous administration, intradermal administration, subcutaneous administration or intramuscular administration. The term "intravenous administration" means administration into a vein. "Intradermal administration" is injection into the upper layer of skin (i.e., the dermis), just beneath the epidermis. "Subcutaneous administration" refers to administration just below the skin. "Intramuscular administration" is the injection directly into a muscle. In preferred embodiments, the injection is in the gluteal muscle or the deltoid muscle.

Antipsychotic Agents

In one embodiment, the compound is a compound of Formula (I):

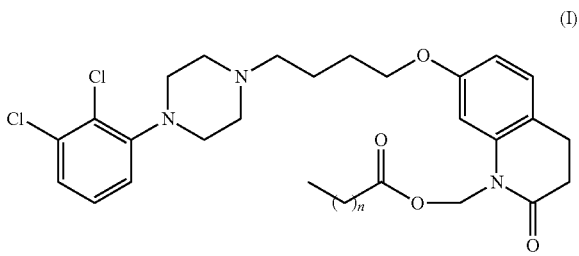

wherein n is an integer between 4 and 14.

In an embodiment, the compound is a compound of Formula (I):

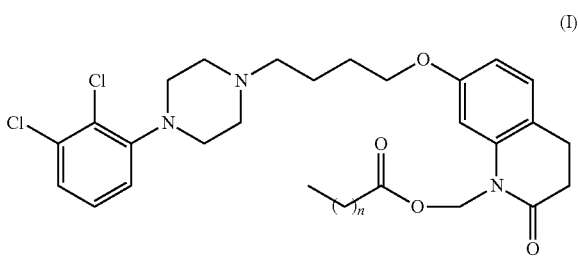

wherein n is an integer between 9 and 11.

In a particular embodiment of Formula (I), n is 4 (Compound A). In another particular embodiment of Formula (I), n is 10 (Compound 1). Compounds A and 1 are depicted below:

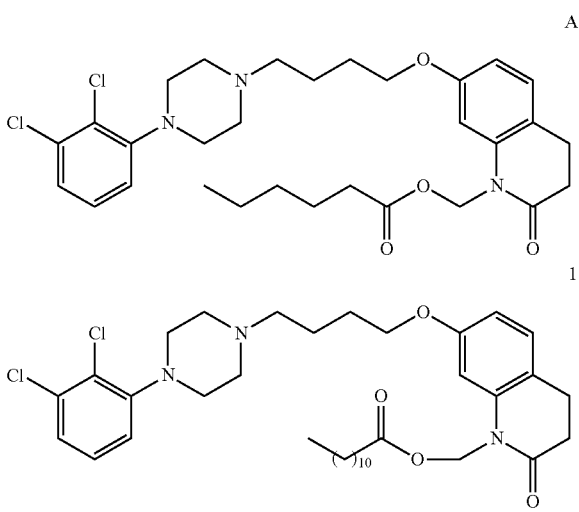

Rapid Injection Speeds

The standard practice for IM adminstration of antipsychotics is to inject medications at a rate that does not exceed 1 mL per 10 seconds or 0.1 mL/s [Cocoman & Murray, Journal of Psychiatric and Mental Health Nursing, 2008, Vol. 15, pp. 424-434]. Healthcare professionals suggest that this slow, steady injection rate promotes patient comfort and helps to avoid damage to the muscle tissue [Workman, Nuring Standard, 1999, Vol. 13, pp. 47-53].

Figure 3:
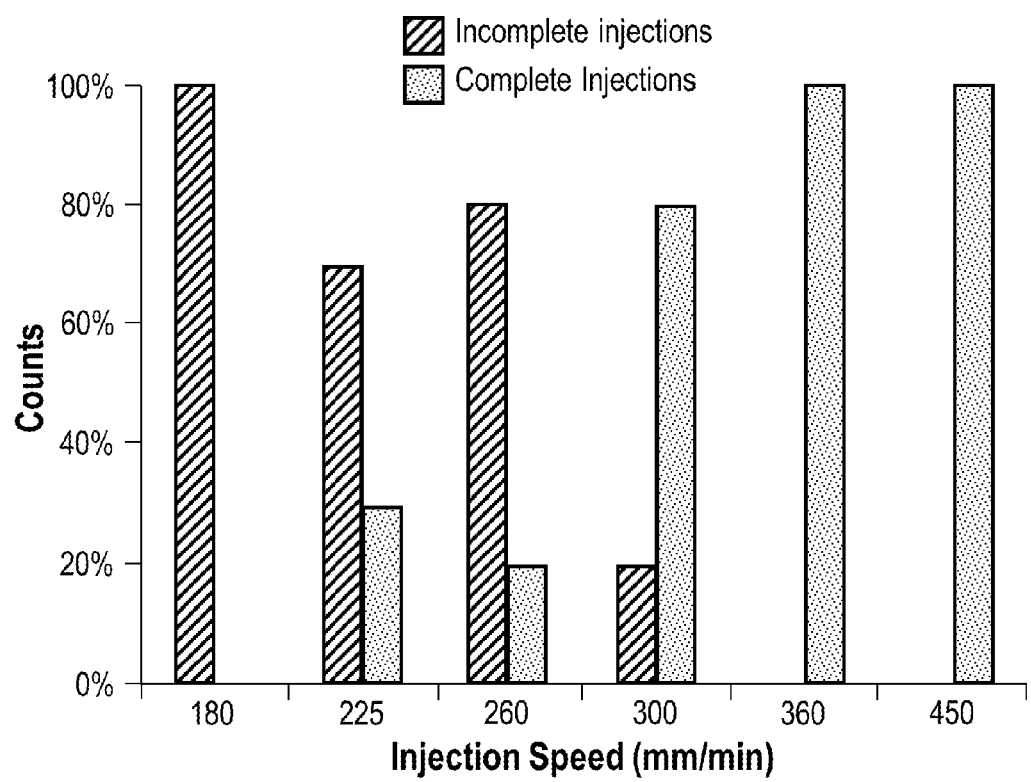
FIG. 3 shows the percentage of incomplete and complete injections of a pharmaceutical composition comprising Compound 1 performed using an INSTRON® at varied injection speeds into an open cell polyurethane foam substrate.
Figure 4A:
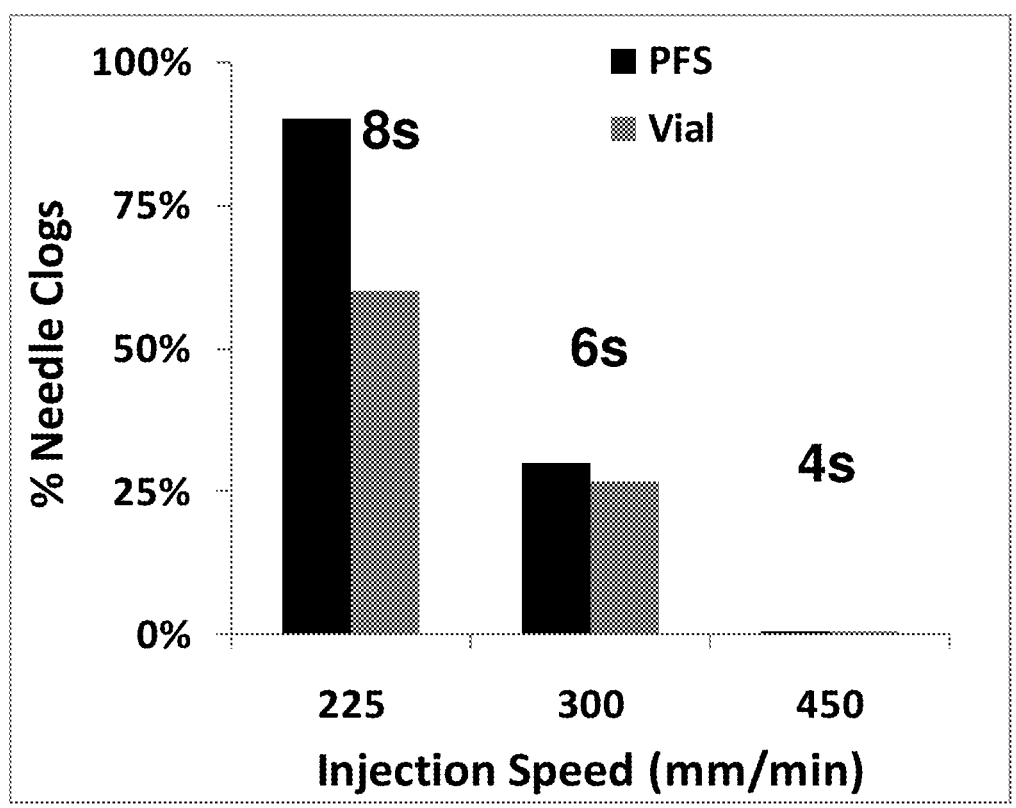
FIGS. 4A and 4B show the occurrence of needle clogs as a function of injection speed upon injection of a pharmaceutical composition comprising Compound 1 into an open cell polyurethane foam substrate.
Figure 4B:
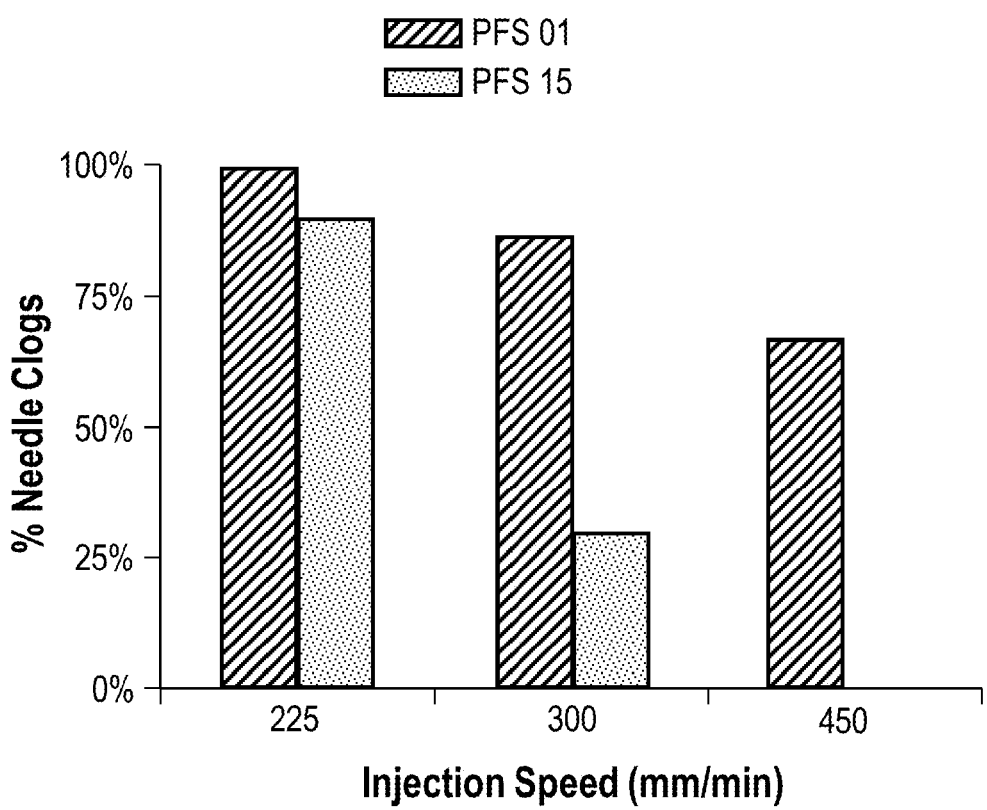

In an effort to prevent needle clogging, manual administration of the pharmaceutical compositions provided herein was performed using faster injection rates. This study surprisingly revealed that the faster the user injected the pharmaceutical compositions provided herein, the less likely the user was to experience a needle clog. These observations are quantitatively supported by the results from injections of the pharmaceutical compositions provided herein performed using an INSTRON® at controlled injection speeds. Indeed, as shown in FIG. 3, faster injection speeds are associated with a decrease in the number of injection clogs whereas slower injection speeds are associated with an increased incidence of needle clogging. Furthermore, Table 6 (Example 3) reveals that increased injection speeds are associated with an increase in measured gravimetric dose delivery and, thus, better flow properties. In fact, manual administration of the pharmaceutical compositions provided herein revealed that slower injection rates were associated with an increased incidence of injection site failure due to needle clogging (see, e.g., FIGS. 3, 4A, and 4B).

Figure 2A:
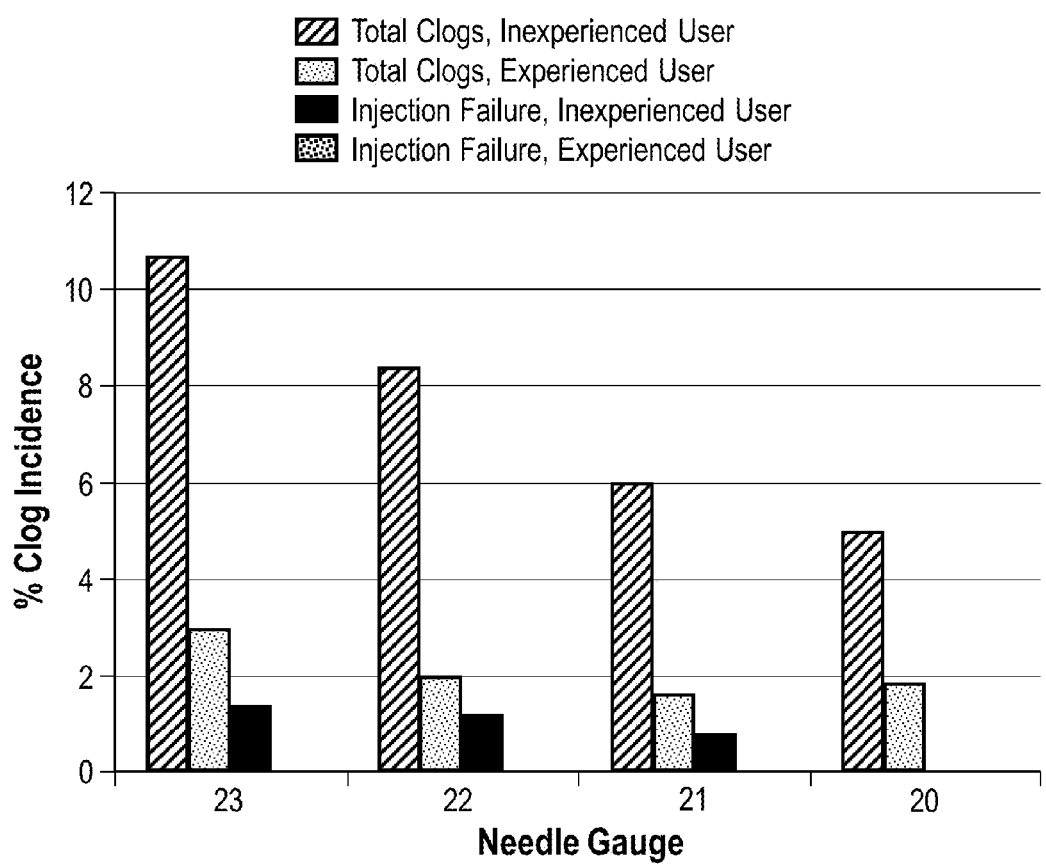
FIGS. 2A and 2B show a summary of needle clog incidence and injection failure as a function of needle gauge upon injection of a pharmaceutical composition comprising Compound 1 into an open cell polyurethane foam substrate.
Figure 2B:
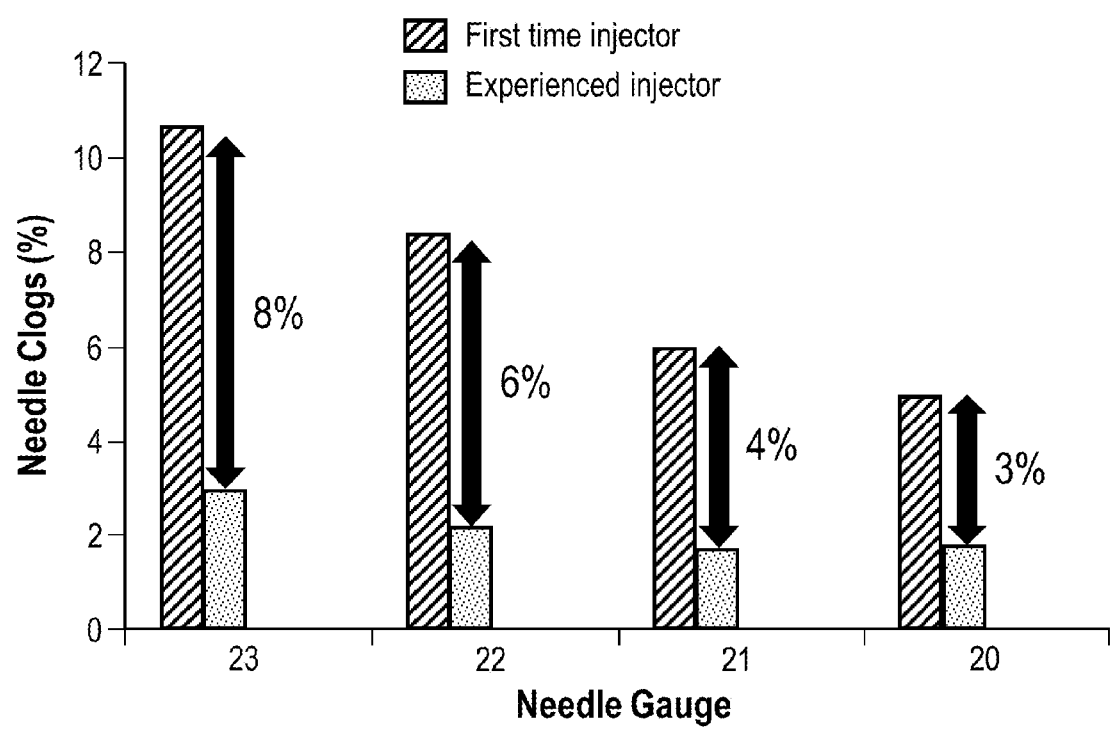

As shown in FIGS. 1, 2A, and 2B, an increase in the incidence of needle clogs was observed with increased needle gauge (i.e., decreased needle inner diameter). Additionally, needle clogs were more pronounced among first time or inexperienced users. Injection failures were also noted primarily with first time users with needle gauges of 21 to 23. No injection failures were noted with experienced users, regardless of needle gauge. Given the results of the in vitro injectability assessment of the pharmaceutical composition administered using various needle gauges, a 20 gauge needle is preferred in order to mitigate the risk of needle clogs.

Rapid injection rates are not typically associated with the injection of drugs due the increased potential for injection site reactions to occur. In fact, the prescribing information for many atypical antipsychotics specifies "slow injection" (see Table 2). Surprisingly, however, it has been discovered that the rapid injection rate of the pharmaceutical compositions provided herein does not elicit injection site reactions or elevated pain intensities (above a normal threshold).

Table 2 summarizes the injection site reactions associated various atypical antipsychotics, including Compound 1. The symptoms of the injection site reaction include, but are not limited to: redness, tenderness, warmth, itching, pain at injection site, blistering, nodule formation, and severe skin damage. Injection site reactions and/or elevated pain levels were reported in patients upon slow injection of ABILIFY MAINTENA® (Aripiprazole Monohydrate), RISPERDAL® CONSTA® (Risperidone), and INVEGA® SUSTENNA® (Paliperidone Palmitate) in comparison with a placebo. In contrast, injection site reactions and/or elevated pain levels were reported in <1% of patients upon fast injection of Compound 1.

TABLE 2

Summary Of Injection Site Reactions (ISRs) Associated With Atypical Antipsychotics*

| Key product features | Compound 1 | ABILIFY MAINTENA ® (Aripiprazole Monohydrate) | RISPERDAL ® CONSTA ® (Risperidone) | INVEGA ® SUSTENNA ® (Paliperidone Palmitate) |
|---|---|---|---|---|
| How Supplied/Administration | Simple DFU, PFS, resuspension Inject rapidly | Multiple step DFU, vial, requires reconstitution, inject immediately Inject Slowly | Multiple step DFU, (it is supplied in a vial) requires reconstitution, in diluent supplied in dose pack (in PFS) Inject entire contents of the syringe intramuscularly into selected gluteal or deltoid muscle | Simple DFU, PFS, homogeneous re-suspension Inject slowly, deep into the muscle. |
| Injection volume | 441 mg: 1.6 mL 662 mg: 2.4 mL 882 mg: 3.2 mL | 400 mg: 2 mL 300 mg: 1.5 mL | 12.5 mg: 2 mL 25 mg: 2 mL 50 mg: 2 mL | 39 mg: 0.25 mL 78 mg: 0.50 mL 117 mg: 0.75 mL 156 mg: 1.00 mL 234 mg: 1.50 mL |
| Formulation | Flocculated suspension | Lyophilized powder | Polymer encapsulated micropsheres | Nano-crystal suspension |
| ISR/Pain rate | ISR: <1% Example 5 | Patient reported: ISR: 6.3% (no placebo) Investigator reported: Redness, Induration, Swelling, pain present in 4-26% of patients (first to last injection) | Patient reported: ISR: no moderate or severe reactions were observed in any subject Investigator reported: mild redness, swelling or induration in (first to last injection) | Patient reported: ISR: Redness, Induration, Swelling, >5% (occurring twice as often as placebo) |
| Needle gauge/length | 20G, 1.5 in & 2 in 21G, 1 in | 21G, 1.5 in & 2 in | 20 G TW, 2 inch gluteal 21 G UTW, 1 inch deltoid | 22 G, 1.5 inch gluteal 22 G, 1.5 inch > 90 kg or 1 inch 23 G < 90 kg deltoid |

*Information obtained from the prescribing information of ABILIFY MAINTENA ®, RISPERDAL ® CONSTA ®, and INVEGA ® SUSTENNA ®

Accordingly, provided herein are methods for intramuscular administration of a pharmaceutical composition to a subject in need thereof, comprising administering to said subject a therapeutically effective amount of the composition at an injection rate greater than or equal to 0.3 mL/s, wherein the pharmaceutical composition is as defined above. In some embodiments, the injection rate is greater than 0.3 mL/s. In particular embodiments, the injection rate is greater than about 0.35 mL/s, or greater than about 0.4 mL/s, greater than about 0.5 mL/s, or greater than about 0.6 mL/s, or greater than about 0.7 mL/s, or greater than about 0.8 mL/s, or greater than 0.9 mL/s. In some embodiments, the injection rate is in the range of from about 0.3 mL/s to about 1 mL/s.

In some embodiments of the method, the pharmaceutical composition is injected using a 20 to 23 gauge needle. In other embodiments of the method, the needle is a 20 gauge needle. In other embodiments of the method, the needle is a 21 gauge needle. In particular embodiments, the needle does not experience injection failure due to needle clogging.

In particular embodiments of the method, a 20 to 23 gauge needle is used to intramuscularly administer a therapeutically effective amount of the composition at an injection rate greater than or equal to 0.3 mL/s, wherein the pharmaceutical composition is as defined above.

In some embodiments, the method does not elicit any injection site reactions in the subject.

In some embodiments of the method, the injection is administered to the subject in the dorsal gluteal muscle. In other embodiments of the method, the injection is administered to the subject in the deltoid muscle.

The administration by injection of a preparation comprising a pharmaceutical compound is often required to be performed in a relatively short time and with a relatively high local concentration of the pharmaceutical agent. This practice is generally referred to in the field as "bolus" injection. The term "bolus injection" thus identifies the administration at once (in general within less than few seconds) of a pharmaceutical agent at a high concentration, differently from a gradual administration of the agent (e.g. by means of intramuscular (IM) infusion).

Accordingly, in one embodiment, the method comprises intramuscularly administering a bolus injection of the pharmaceutical composition. In particular embodiments, the bolus injection is administered at a very rapid injection rate. In some embodiments, the bolus injection is injected with an injection rate that is greater than 0.3 mL/s. In other embodiments, the bolus injection is injected instantaneously. In particular embodiments, the needle does not experience injection failure due to needle clogging.

Lyophilization

The pharmaceutical compositions described herein can be formulated in such a way that the active ingredient and the active ingredient-retaining substance may be dissolved in a suitable solvent and subjected to lyophilization (or freeze-drying) to obtain a sterile cake of the active ingredient and the active ingredient-retaining substance.

In one aspect, the pharmaceutical compositions described herein are lyophilized prior to administration. Lyophilization is carried out using techniques common in the art [Tang et al., *Pharm Res.* 2004, 21, 191-200, and Chang et al., *Pharm Res.* 1996, 13, 243-249], and has been optimized for the pharmaceutical composition described herein.

A lyophilization cycle is, in one aspect, composed of three steps: freezing, primary drying, and secondary drying [A. P. Mackenzie, *Phil Trans R Soc London, Ser B, Biol* 1977, 278, 167]. In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

In one aspect, provided herein is a lyophilized cake comprising a pharmaceutical composition, wherein said pharmaceutical composition comprises:

(a) 15-35 weight percent of a compound of Formula (I);
(b) 0.25-0.45 weight percent sorbitan laurate; and
(c) 0.2-1 weight percent polysorbate 20 wherein the percentages of (a), (b), and (c) are relative to the total weight of the composition.

In another embodiment of the lyophilized cake, the pharmaceutical composition comprises:

(a) 24-30 weight percent of a compound of Formula (I);
(b) 0.3-0.4 weight percent sorbitan laurate; and
(c) 0.1-0.3 weight percent polysorbate 20 wherein the percentages of (a), (b), and (c) are relative to the total weight of the composition.

In still another embodiment of the lyophilized cake, the pharmaceutical composition comprises:

(a) about 26.6 weight percent of a compound of Formula (I);
(b) about 0.37 weight percent sorbitan laurate; and
(c) about 0.15 weight percent polysorbate 20 wherein the percentages of (a), (b), and (c) are relative to the total weight of the composition.

In an embodiment of the lyophilized cake, the pharmaceutical composition comprises:

(a) 15-35 weight percent Compound 1:

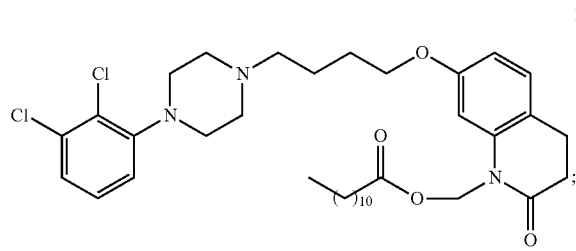

(b) 0.25-0.45 weight percent sorbitan laurate; and
(c) 0.2-1 weight percent polysorbate 20 wherein the percentages of (a), (b), and (c) are relative to the total weight of the composition.

In another embodiment of the lyophilized cake, the pharmaceutical composition comprises:

(a) 24-30 weight percent Compound 1:

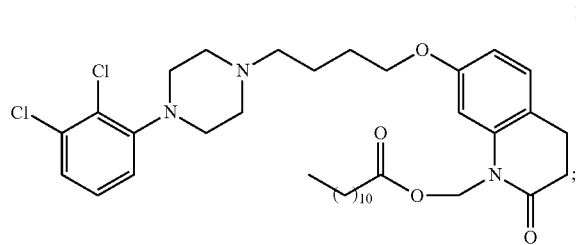

(b) 0.3-0.4 weight percent sorbitan laurate; and
(c) 0.1-0.3 weight percent polysorbate 20 wherein the percentages of (a), (b), and (c) are relative to the total weight of the composition.

In still another embodiment of the lyophilized cake, the pharmaceutical composition comprises:

(a) about 26.6 weight percent Compound 1:

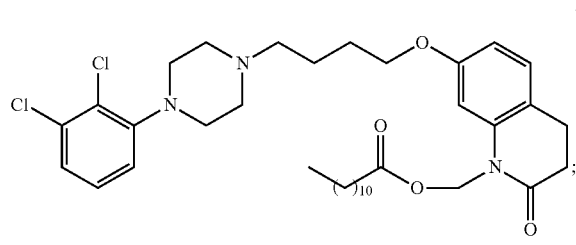

(b) about 0.37 weight percent sorbitan laurate; and
(c) about 0.15 weight percent polysorbate 20 wherein the percentages of (a), (b), and (c) are relative to the total weight of the composition.

In some embodiments, the lyophilized cake comprises approximately 1400 mg of the pharmaceutical composition. In preferred embodiments, the compound of Formula (I) is Compound 1.

In some embodiments, the lyophilized cake is reconstituted in an aqueous vehicle (e.g., sterile water for injection, an aqueous buffer, or saline solution). In particular embodiments, the lyophilized cake is reconstituted in 3.0 mL of an aqueous vehicle (e.g., sterile water for injection, an aqueous buffer, or saline solution). In particular embodiments, the lyophilized cake is reconstituted in 2.5 mL of an aqueous vehicle (e.g., sterile water for injection, an aqueous buffer, or saline solution). In particular embodiments, the lyophilized cake is reconstituted in 2.0 mL of an aqueous vehicle (e.g., sterile water for injection, an aqueous buffer, or saline solution). In some embodiments, the lyophilized cake can be reconstituted for injection within 1-60 seconds of handshaking. In preferred embodiments, the lyophilized cake can be reconstituted for injection within 10-20 seconds of handshaking.

In one embodiment, the lyophilized cake of the pharmaceutical composition is administered as part of a bolus injection.

In one aspect, provided herein is a method for preparing a lyophilized cake of the pharmaceutical compositions provided herein.

In one embodiment, during the lyophilization process, the solvent system used, such as by way of example only, sterile water for injection is substantially removed by sublimation. In another embodiment, less than about 5% residual solvent remains after lyophilization; in other embodiments, less than about 3% remains; in yet other embodiments, less than about 2% remains; in further embodiments, less than about 1% or about 0.1% remains.

In one embodiment, the lyophilization process comprises the steps of: (1) placing the sample to be lyophilized (i.e., the pharmaceutical composition comprising a compound of Formula (I), sorbitan laurate, and polysorbate 20) in a suitable vial and placing the vial into a lyophilization chamber frozen in a bath until suspension was solidified; (2) cooling the lyophilization chamber and reducing the pressure of the system; and holding until sublimation of the solvent system is substantially complete; and (3) slowly increasing the temperature of the lyophilization chamber to allow the samples to reach an elevated shelf temperature.

In another embodiment, the lyophilization process comprises the steps of: (1) placing the sample to be lyophilized (i.e., the pharmaceutical composition comprising a compound of Formula (I), sorbitan laurate, and polysorbate 20) in a suitable vial and placing the vial into a lyophilization chamber frozen in a methanol-dry ice bath until suspension was solidified; (2) cooling the lyophilization chamber to −75° C. and reducing the pressure of the system to below 100 mTorr; and holding until sublimation of the solvent system is substantially complete (about 72 hours); and (3) slowly increasing the temperature of the lyophilization chamber to allow the samples to reach a temperature of about 20° C. to about 30° C.

In one embodiment, the lyophilized cake is in a container, and the aqueous vehicle is in a separate container, wherein said container is any receptacle and closure therefor suitable for storing, shipping, dispensing, and/or handling a pharmaceutical product. Examples of such containers include, at least, for example, plastic and glass vials, ampules, pre-filled syringes and cartridges, and the like.

In some embodiments, pre-filled dual-chamber syringes and/or cartridges are utilized with the lyophilized cakes provided herein. The dual-chamber syringe can accommodate lyophilized, powder in the front chamber combined with the aqueous vehicle in the rear chamber.

Prefilled syringes can contain the exact deliverable dose of desired the pharmaceutical compositions provided herein.

The prefilled syringes can contain volumes from about 0.1 mL, 0.2 mL, 0.3 mL, 0.4 mL, 0.5 mL, 0.6 mL, 0.7 mL, 0.8 mL, 0.9 mL, 1.0 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL or more or any other volume increment thereof.

The dual syringe and/or cartridge can be side-by-side chambers with separate syringe plungers that mix into a single chamber or linear chambers with one plunger. The dual chamber syringe and/or cartridges can also have a stopper or connector in the middle to serve as a barrier between the two chambers. The stopper or connector can be removed to allow mixing or combining of the compounds in the two chambers. For example, the front chamber can accommodate the lyophilized cake provided herein, and the rear chamber can accommodate the aqueous vehicle. Thus, in one embodiment, pre-filled dual-chamber syringe contains the lyophilized cake provided herein in the front chamber and the aqueous vehicle in the rear chamber.

Methods of Treatment

The pharmaceutical compositions of the methods provided herein can be used for the treatment of a variety of disorders in a subject in need thereof. For example, the pharmaceutical compositions described herein can be used to treat anxiety, depression, bipolar disorder, autism-related irritability, and psychotic conditions including acute mania, schizophrenia, and schizophreniform disorder in a subject. In another embodiment, the pharmaceutical compositions of the methods provided herein can be used to treat bipolar disorder-related agitation and schizophrenic-related agitation.

In one aspect, provided herein is a method of treating a disorder of the central nervous system in a subject in need thereof, comprising administering to said subject a therapeutically amount of the composition at an intramuscular injection rate greater than or equal to 0.3 mL/s, wherein said pharmaceutical composition comprises:

(a) 15-35 weight percent of a compound of Formula (I):

(b) 0.25-0.45 weight percent sorbitan laurate;

(c) 0.2-1 weight percent polysorbate 20; and (d) an aqueous vehicle wherein the percentages of (a), (b), and (c) are relative to the total weight of the composition.

In one embodiment of the method of treatment, the pharmaceutical composition comprises:

(a) 24-30 weight percent of a compound of Formula (I);

(b) 0.3-0.4 weight percent sorbitan laurate;

(c) 0.1-0.3 weight percent polysorbate 20; and (d) an aqueous vehicle wherein the percentages of (a), (b), and (c) are relative to the total weight of the composition.

In another embodiment of the method of treatment, the pharmaceutical composition comprises:

(a) about 26.6 weight percent of a compound of Formula (I);

(b) about 0.37 weight percent sorbitan laurate;

(c) about 0.15 weight percent polysorbate 20; and (d) an aqueous vehicle wherein the percentages of (a), (b), and (c) are relative to the total weight of the composition.

In still embodiment of the method of treatment, the pharmaceutical composition comprises:
(a) 15-35 weight percent of Compound 1:

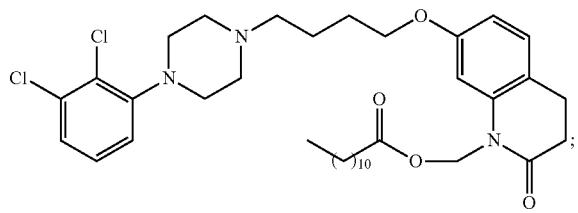

(b) 0.25-0.45 weight percent sorbitan laurate;
(c) 0.2-1 weight percent polysorbate 20; and
(d) an aqueous vehicle
wherein the percentages of (a), (b), and (c) are relative to the total weight of the composition.

In yet another embodiment of the method of treatment, the pharmaceutical composition comprises:
(a) 24-30 weight percent of Compound 1:

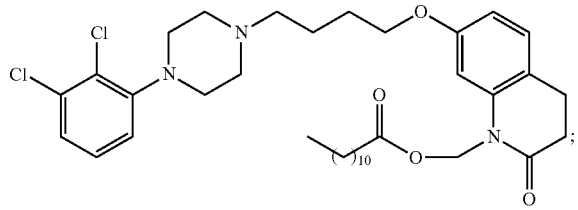

(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition.

In one embodiment of the method of treatment, the pharmaceutical composition comprises:
(a) about 26.6 weight percent of Compound 1:

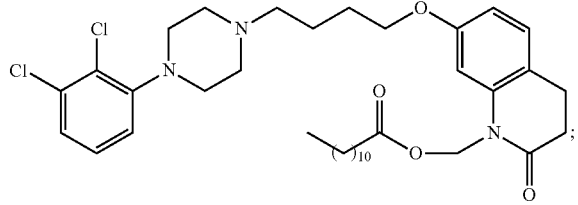

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

In an embodiment of all these methods, the method comprises administering to a subject in need thereof a therapeutically effective amount of the composition at an injection rate greater than or equal to 0.3 mL/s. In particular embodiments, the injection rate is greater than about 0.35 mL/s, or greater than about 0.4 mL/s, greater than about 0.5 mL/s, or greater than about 0.6 mL/s, or greater than about 0.7 mL/s, or greater than about 0.8 mL/s, or greater than 0.9 mL/s. In some embodiments, the method of administration is intramuscular.

In another embodiment, the pharmaceutical composition comprises:
(a) 24-30 weight percent of a compound of Formula (I):

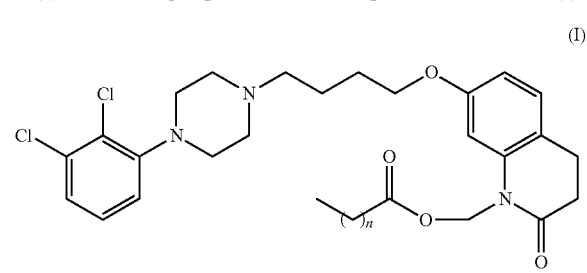

wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition, for use in therapy by intramuscular administration at an injection rate greater than or equal to 0.3 mL/s.

In yet another embodiment, the pharmaceutical composition comprises:
(a) 24-30 weight percent of Compound 1:

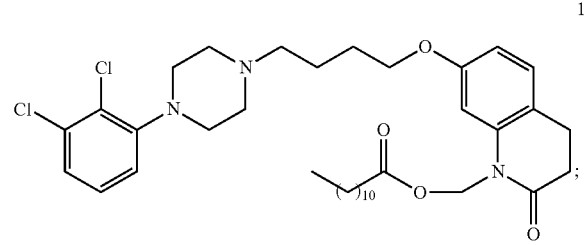

(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition, for use in therapy by intramuscular administration at an injection rate greater than or equal to 0.3 mL/s.

In still another embodiment, the pharmaceutical composition comprises:
(e) 24-30 weight percent of a compound of Formula (I):

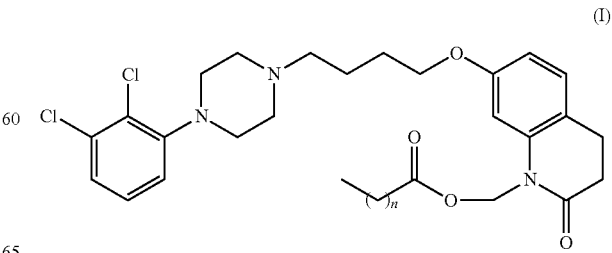

wherein n is an integer between 4 and 14;

(f) 0.3-0.4 weight percent sorbitan laurate;
(g) 0.1-0.3 weight percent polysorbate 20; and
(h) an aqueous vehicle wherein the percentages of (a), (b), and (c) are relative to the total weight of the composition, for use in a method of treating a disorder of the central nervous system, wherein the composition is intramuscularly administered at an intramuscular injection rate greater than or equal to 0.3 mL/s.

In another embodiment, the pharmaceutical composition comprises:

(a) 24-30 weight percent of Compound 1:

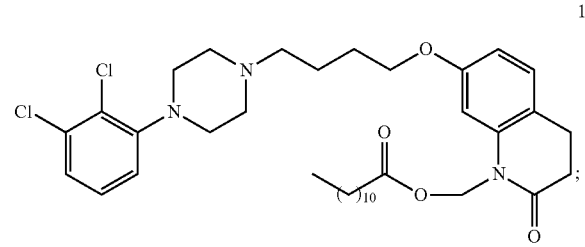

(b) 0.3-0.4 weight percent sorbitan laurate;
(c) 0.1-0.3 weight percent polysorbate 20; and
(d) an aqueous vehicle wherein the percentages of (a), (b), and (c) are relative to the total weight of the composition, for use in a method of treating a disorder of the central nervous system, wherein the composition is intramuscularly administered at an intramuscular injection rate greater than or equal to 0.3 mL/s.

In certain embodiments of the method of treating a disorder of the central nervous system, the method is for maintenance treatment. In other embodiments of the method, the method is for acute treatment.

In some embodiments of the method, the disorder of the central nervous system is schizophrenia, bipolar I disorder, or autistic disorder. In one embodiment of the method, the disorder is schizophrenia. In another embodiment of the method, the disorder is schizophreniform disorder.

In particular embodiments of the method, the intramuscular injection rate is greater or equal to than 0.3 mL/s. In other embodiments of the method, the intramuscular injection rate is greater than 0.3 mL/s.

In one embodiment, a therapeutically effective amount of the agent is given to a subject using the pharmaceutical compositions provided herein. The term "therapeutically effective amount" is further meant to define an amount resulting in the improvement of any parameters or clinical symptoms. The actual dose may vary with each patient and does not necessarily indicate a total elimination of all disease symptoms. In the case of antipsychotics, the management of exacerbations and maintenance of remission of psychiatric symptoms are main goals of therapy, and selection of the appropriate drug and dosage in a particular disease balances these goals with the minimization of adverse events attributable to the drug.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred suitable dosages for the compounds used in the treatment described herein are on the order of about 1 mg to about 600 mg preferably about 3, 5, 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total of active agent. Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition used in the treatment described herein can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth. Unit dose preparations provided herein can contain a compound of Formula (I) in the range of about 20 to about 900, e.g., about 60 to about 800, mgs (aripiprazole base equivalents).

Preferred amounts according to the selected mode of administration are able to be determined by one skilled in the art. Pharmaceutical compositions can be manufactured utilizing techniques known in the art. Typically the therapeutically effective amount of the compound will be admixed with a pharmaceutically acceptable carrier.

Kits

Advantageously, the present invention relates to a kit comprising a unit dosage of the pharmaceutical composition of the methods disclosed herein.

In one aspect, provided herein is a kit useful for the treatment of a disorder of the central nervous system, comprising a therapeutically effective amount of a pharmaceutical composition and further comprising instructions for intramuscular injection, wherein the intramuscular injection rate is greater than or equal to 0.3 mL/s, wherein said pharmaceutical composition comprises:

(a) a compound of Formula (I):

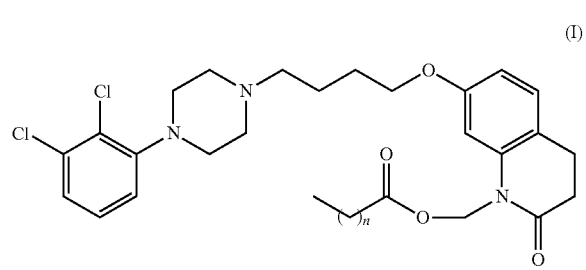

wherein n is an integer between 4 and 14;
(b) sorbitan laurate;
(c) polysorbate 20; and
(d) an aqueous vehicle wherein the percentages of (a), (b), and (c) are relative to the total weight of the composition.

In one embodiment, the pharmaceutical composition comprises:

(b) a compound of Formula (I):

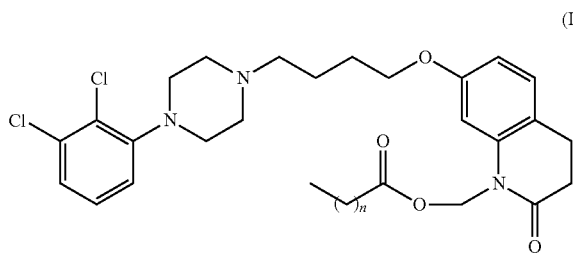

wherein n is an integer between 9 and 11;
(b) sorbitan laurate;
(c) polysorbate 20; and
(d) an aqueous vehicle wherein the percentages of (a), (b), and (c) are relative to the total weight of the composition.

In another embodiment of the kit, the pharmaceutical composition comprises:

(a) 24-30 weight percent of a compound of Formula (I):

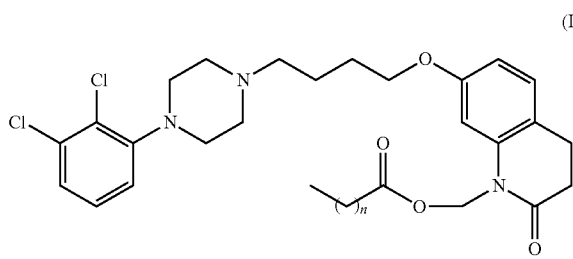

wherein n is an integer between 4 and 14;
(b) 0.3-0.4 weight percent sorbitan laurate;
(c) 0.1-0.3 weight percent polysorbate 20; and
(d) an aqueous vehicle wherein the percentages of (a), (b), and (c) are relative to the total weight of the composition.

In another embodiment of the kit, the pharmaceutical composition comprises:

(a) 24-30 weight percent of a compound of Formula (I):

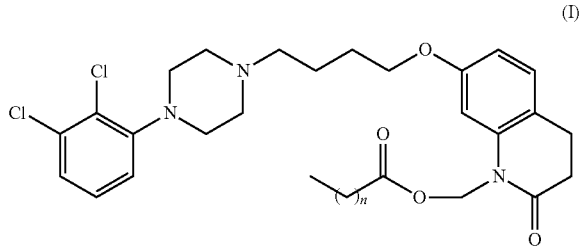

wherein n is an integer between 9 and 11;
(b) 0.3-0.4 weight percent sorbitan laurate;
(c) 0.1-0.3 weight percent polysorbate 20; and
(d) an aqueous vehicle wherein the percentages of (a), (b), and (c) are relative to the total weight of the composition.

In still another embodiment of the kit, the pharmaceutical composition comprises:

(a) about 26.6 weight percent a compound of Formula (I):

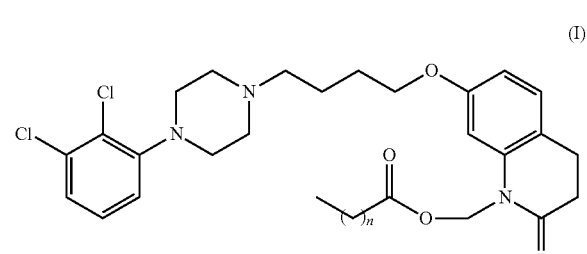

wherein n is an integer between 4 and 14;
(b) about 0.37 weight percent sorbitan laurate;
(c) about 0.15 weight percent polysorbate 20; and
(d) an aqueous vehicle wherein the percentages of (a), (b), and (c) are relative to the total weight of the composition.

In still another embodiment of the kit, the pharmaceutical composition comprises:

(a) about 26.6 weight percent a compound of Formula (I):

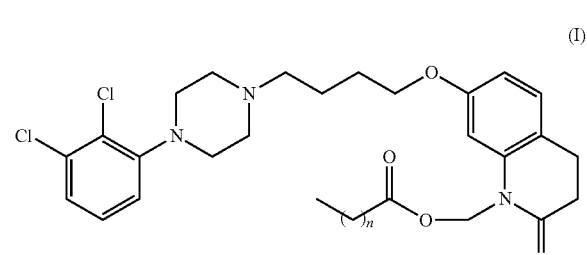

wherein n is an integer between 9 and 11;
(b) about 0.37 weight percent sorbitan laurate;
(c) about 0.15 weight percent polysorbate 20; and
(d) an aqueous vehicle wherein the percentages of (a), (b), and (c) are relative to the total weight of the composition.

In another aspect, provided herein is a kit useful for the treatment of a disorder of the central nervous system, comprising a therapeutically effective amount of a pharmaceutical composition and further comprising instructions for intramuscular injection, wherein the intramuscular injection rate is greater than or equal to 0.3 mL/s, wherein said pharmaceutical composition comprises:

(a) 15-35 weight percent of Compound 1:

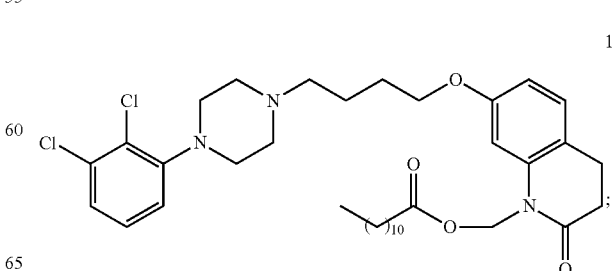

(b) 0.25-0.45 weight percent sorbitan laurate;
(c) 0.2-1 weight percent polysorbate 20; and
(d) an aqueous vehicle wherein the percentages of (a), (b), and (c) are relative to the total weight of the composition.

In another embodiment of the method, the pharmaceutical composition comprises:
(a) 24-30 weight percent Compound 1:

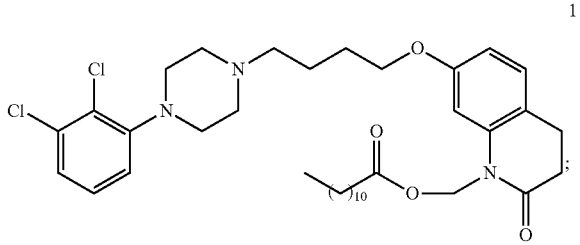

(b) 0.3-0.4 weight percent sorbitan laurate;
(c) 0.1-0.3 weight percent polysorbate 20; and
(d) an aqueous vehicle wherein the percentages of (a), (b), and (c) are relative to the total weight of the composition.

In still another embodiment of the method, the pharmaceutical composition comprises:
(a) about 26.6 weight percent of Compound 1:

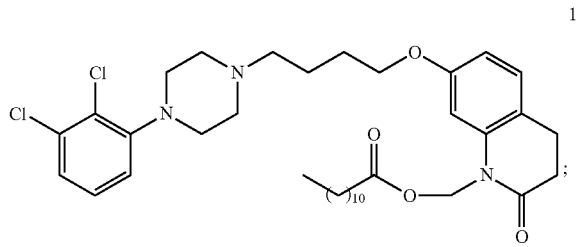

(b) about 0.37 weight percent sorbitan laurate;
(c) about 0.15 weight percent polysorbate 20; and
(d) an aqueous vehicle wherein the percentages of (a), (b), and (c) are relative to the total weight of the composition.

In some embodiments, the kit is adapted to be associated with a treatment regimen. In preferred embodiments of the kit, the intravenous injection rate is greater than 0.3 mL/s.

In some embodiments of the kit, the instructions are for intramuscular injection, wherein the intramuscular injection rate is rapid or instantaneous. In other preferred embodiments of the kit, the instructions are for intramuscular injection, wherein the intramuscular injection rate is greater than 0.3 mL/s. In certain embodiments, the injection rate is greater than about 0.35 mL/s, or greater than about 0.4 mL/s, greater than about 0.5 mL/s, or greater than about 0.6 mL/s, or greater than about 0.7 mL/s, or greater than about 0.8 mL/s, or greater than 0.7 mL/s, or greater than 0.8 mL/s, or greater than 0.9 mL/s. In an embodiment, the instructions are for administering approximately 3.4 mL of the pharmaceutical composition within 10 seconds. In another embodiment, the instructions are for administering approximately 1.6 mL of the pharmaceutical composition within 5 seconds.

In yet another embodiment of the kit, the instructions are for administering the injection to the subject in the dorsal gluteal muscle. In an embodiment of the kit, the instructions are for administering the injection to the subject in the deltoid muscle.

A "kit" as used in the instant application includes a container for containing the separate unit dosage forms such as a glass vial or prefilled syringe (PFS). The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container). The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

In some embodiments, the kit includes a 20 to 23 gauge needle. In other embodiments of the kit, the needle is a 20 gauge needle. In other embodiments of the kit, the needle is a 21 gauge needle.

Definitions

The terms "treat", "treated", "treating", or "treatment" includes the diminishment or alleviation of at least one symptom associated or caused by the state, disorder or disease being treated. For example, treatment can be diminishment of one or several symptoms of a disorder or complete eradication of a disorder.

The term "weight percent" is meant to refer to the quantity by weight of a compound and/or component in a composition as the quantity by weight of a constituent component of the composition as a percentage of the weight of the total composition. The weight percent can also be calculated by multiplying the mass fraction by 100. The "mass fraction" is the ratio of one substance of a mass $m_1$ to the mass of the total composition $m_t$.

$$\text{weight percent} = (m_1/m_t)*100$$

As used herein, the term "modulating" or "modulate" refers to an effect of altering a biological activity, especially a biological activity associated with an injection site reaction.

The term "use" includes any one or more of the following embodiments of the invention, respectively: the use in the treatment of pain the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, inflammation, cardiac hypertrophy, and HIV infection, and other diseases or conditions described herein (e.g., a protein kinase-associated disorder). In another embodiment, the subject is a cell.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition.

As used herein, the term "pharmaceutically acceptable carrier", and cognates thereof, refers to adjuvants, binders, diluents, etc. known to the skilled artisan that are suitable for administration to an individual (e.g., a mammal or non-mammal). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutical compositions described herein include at least one pharmaceutically acceptable carrier or excipient; preferably, such compositions include at least one carrier or excipient other than or in addition to water.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

As used herein and in the appended claims, the singular forms "a", "an", and "the" include plural forms, unless the context clearly dictates otherwise.

Unless defined otherwise or clearly indicated by context, all technical and scientific terms used herein have the same meaning as commonly understood by one of ordinary skill in the art to which this invention belongs.

All relevant preferred features and embodiments apply to each of the claims and statements of invention mentioned above.

EXEMPLIFICATION

Example I

Synthesis Procedures

Synthesis of Compound 1

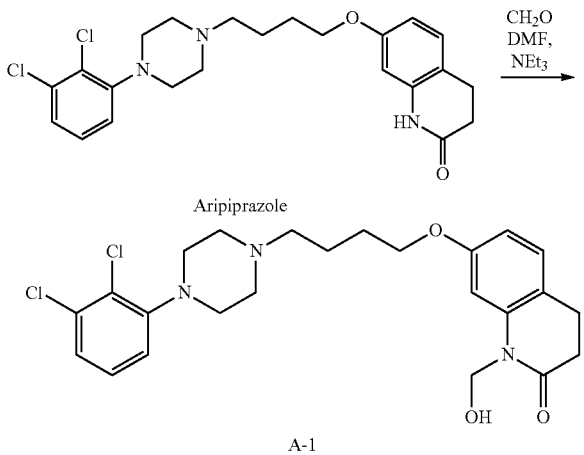

Compound A-1: Preparation of 7-(4-(4-(2,3-dichlorophenyl)piperazin-1-yl)butoxy)-1-(hydroxymethyl)-3,4-dihydroquinolin-2(1H)-one A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over $MgSO_4$, filtered and evaporated to dryness under vacuum to give hemi-aminal A-1 as a white solid (18.6 g, containing 25% Aripiprazole, 65% yield based on A-1).

Compound 1a: (7-(4-(4-(2,3-dichlorophenyl)piperazin-1-yl)butoxy)-2-oxo-3,4-dihydroquinolin-1(2H)-yl)methyl acetate

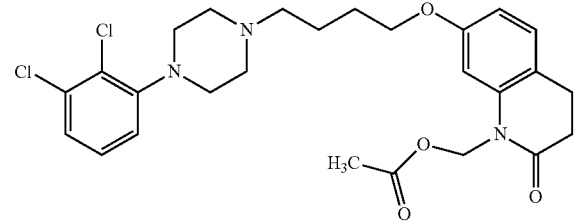 [SMILES: CC(=O)OCN1C(=O)CCc2ccc(OCCCCN3CCN(c4cccc(Cl)c4Cl)CC3)cc21]

A solution of Compound A-1 (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO₃ (5% aqueous solution, 250 mL). After separation of the two layers, pH of the aqueous layer was adjusted to above 7. The aqueous layer was further extracted using the organic mixture. The organic layer was separated and washed with 5% NaHCO₃ solution, followed by deionized water, and brine. The solution was dried using anhydrous MgSO₄, filtered and evaporated under vacuum. The resulting product was purified using silica gel column chromatography using ethanol:ethyl acetate (5:95) as the eluent. Fractions containing the desired product were combined and d-tartaric acid (12.5 g dissolved in 60:5 ethanol:water) was added, resulting in the precipitation of the desired product (48.78 g, 89% yield). ¹H NMR (CDCl3, 300 MHz) δ1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

Compound 1: (7-(4-(4-(2,3-dichlorophenyl)piper-azin-1-yl)butoxy)-2-oxo-3,4-dihydroquinolin-1(2H)-yl)methyl dodecanoate

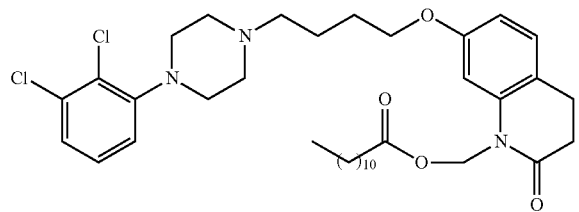

Compound 1 was prepared in an analogous fashion to Compound 1a. The desired product was isolated as a crystalline solid (0.3 g, 21% yield). The molecular weight was confirmed by mass spectrometer analysis. ¹H NMR (CDCl3, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H).

Compound A-28: (7-(4-(4-(2,3-dichlorophenyl)pip-erazin-1-yl)butoxy)-2-oxo-3,4-dihydroquinolin-1 (2H)-yl)methyl benzylcarbamate

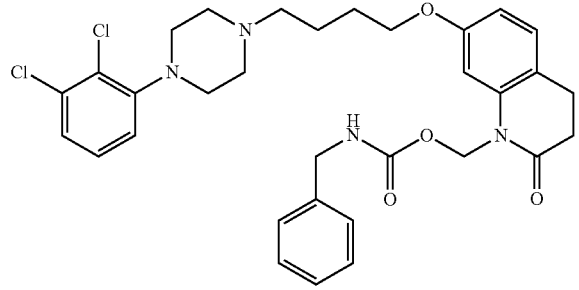 [SMILES: O=C(NCc1ccccc1)OCN1C(=O)CCc2ccc(OCCCCN3CCN(c4cccc(Cl)c4Cl)CC3)cc21]

To a solution of hemi-aminal A-1 (4 g, 8.4 mmol), 4-dimethylaminopyridine (0.15 g, 1.3 mmol) and triethyl-amine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO₄, filtered and evaporated under vacuum. The residue was further purified by chromatography on silica eluting with ethyl acetate/dichloromethane/methanol (1:1:0.1) to give the desired product as an off white foam (530 mg, 14% yield). ¹H NMR (CDCl₃, 300 MHz) δ 1.58-1.88 (m, 4H), 2.48 (t, 2H), 2.60-2.72 (m, 6H), 2.85 (m, 2H), 3.00-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M⁺H) 611.12 and 613.10.

Compound A: (7-(4-(4-(2,3-dichlorophenyl)piper-azin-1-yl)butoxy)-2-oxo-3,4-dihydroquinolin-1(2H)-yl)methyl hexanoate

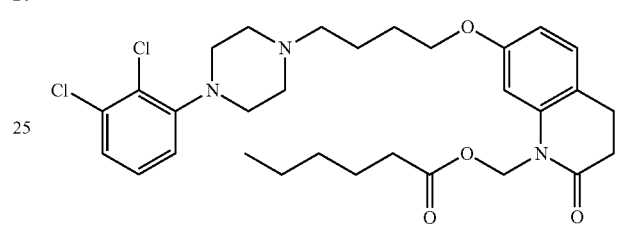

Compound A was prepared in an analogous fashion to Compound A-28. The desired product was isolated as a yellow solid (3.69 g, 87% yield). ¹H NMR (CDCl₃, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M⁺H) 576.4 and 578.4.

Example II

Exemplary Formulations

TABLE 3

Example formulation of the invention.

| Formulation | Amount Per Dose (% w/w) |
|---|---|
| Compound 1 | 26.6 |
| Sorbitan monolaurate | 0.37 |
| Polysorbate 20 | 0.15 |
| Sodium Chloride | 0.59 |
| CMC | NA |
| Sodium Phosphate Dibasic Anhydrous | 0.06 |
| Sodium Dihydrogen Phosphate Monobasic Dihydrate | 0.05 |
| Water for Injection | QS to 100 | pH range: 5.0-7.4

Example III

In vitro Assessments of Compound 1 PFS Product Performance when Administered Using Various Needle Gauges and at Varied Injection Speeds An in vitro assessment was carried out with an pre-filled syringe (PFS) containing the formulation of Example II.

Product performance was assessed by measuring the amount of drug product that was injected after resuspension into a foam resistance model (gravimetric dose delivery with applied resistance). The drug product was injected into open cell (250 to 300 µm pore size) polyurethane foam and the gravimetric delivered dose is measured. The injection was performed manually by either users who were categorized as experienced or inexperienced or by an INSTRON® universal testing machine at constant injection speed (INSTRON®, Norwood, Mass.). An experienced user is defined as those that have conducted injections of the Compound 1 drug product previously, such as, physicians or lab analysts. An inexperienced user is defined as personnel that are not lab analysts or those that have never conducted injections of the Compound 1 drug product. Mean inner diameters for needle gauges used in this experiment are listed in Table 4.

TABLE 4

Terumo Needle Gauge and
Mean Internal Needle Diameter Needle

| Needle Gauge | Internal Needle Diameter (µm) |
|---|---|
| 23 | 405 |
| 22 | 485 |
| 21 | 575 |
| 20 | 660 |

Manual in vitro Assessment of PFS Injectabilty:

A total of 1460 injections by 44 users were completed according to the following primary steps:

1. Resuspend the syringe contents by shaking vigorously for ~30 seconds
2. Attach needle to the syringe
3. Prime the syringe by bringing it into an upright position, tap the syringe to bring air to the top and then carefully depress the plunger rod until ~1-2 drops of suspension are released
4. Inject the full contents into foam in a rapid and continuous manner (<10 seconds)
5. If a clog occurs, replace the needle and attempt to complete the injection. If a second clog occurs, continue to the next step
6. Record the weight of the suspension following completion of the injection to determine gravimetric dose delivery.

Each user was given a spare needle in the event of a needle clog. Each needle clog was recorded as were injection failures (defined by inability to deliver entire contents of a syringe following use of the spare (2nd) needle).
In vitro Assessment of PFS Injectabilty Using an INSTRON® Universal Materials Tester in Compression Mode at Varied Injection Speeds:

Ten injections were performed at each injection speed according to the following primary steps:

1. Resuspend the syringe contents on a Burrel wrist action shaker for 30 Seconds.
2. Prime the syringe by bringing it into an upright position, tap the syringe to bring air to the top and then carefully depress the plunger rod until ~1-2 drops of suspension are released.
3. Place the syringe in the INSTRON® syringe test fixture.
4. Inject the contents of the syringe into the foam at constant injection speed to max force of 40 N.
5. Record the weight following completion of the injection to determine gravimetric dose delivery.

One needle replacement was allowed per syringe tested. Each needle clog was recorded as were injection failures (defined by inability to deliver entire contents of a syringe following use of the spare (2nd) needle).
Manual in vitro Assessment of Compound 1 PFS Injectability A summary of needle clogs as a function of needle gauge and user experience is shown in FIG. 1. A summary of needle clog incidence and injection failures as a function of needle gauge and user experience is shown in FIGS. 2A and 2B. Measured gravimetric dose delivery was compared to the expected dose delivery of the high dose. Gravimetric dose delivery results and number of injections that delivered less than 75% of expected as a function of needle gauge for all users are summarized in Table 5.

TABLE 5

In Vitro Assessment of Injectability by Gravimetric Dose Delivery

| Needle Gauge | Total Number of Injections | Number (%) of Injections less than 75% of expected dose delivery | Gravimetric Dose Delivery (g), Average ± SD |
|---|---|---|---|
| 23 | 390 | 4 (1.0%) | 3.41 ± 0.15 |
| 22 | 350 | 3 (0.9%) | 3.41 ± 0.19 |
| 21 | 370 | 1 (0.3%) | 3.42 ± 0.11 |
| 20 | 350 | 0 (0%) | 3.41 ± 0.05 |

In vitro Assessment of PFS Injectabilty Using an INSTRON®

A summary of incomplete and complete injections performed using the INSTRON® at varied injection speeds is shown in FIG. 3. A summary of the resultant gravimetric dose delivery results is shown in Table 6.

TABLE 6

Gravimetric Dose Delivery Results From Injections
Performed Using an INSTRON ® at Varied Injection Speeds

| Injection Speed | Gravimetric Dose Delivery (g), Average ± SD |
|---|---|
| 180 | 0.99 ± 0.37 |
| 225 | 2.26 ± 0.86 |
| 260 | 2.81 ± 0.51 |
| 300 | 3.23 ± 0.12 |
| 360 | 3.27 ± 0.05 |
| 450 | 3.30 ± 0.03 |

Example IV

Exemplary Suspension Lyophilization for Increased Dose

Suspension
Lyophilization:
1. Re-suspended Compound 1 injectable suspension (i.e., the formulation of Example II) was pooled into BD 50 mL polypropylene conical tube. Total twenty PFS were pooled into four conical tubes.
2. Conical tubes were frozen in a methanol-dry ice bath until suspension was solidified. Tubes were allowed to freeze further 15 min to ensure complete freezing of a suspension.
3. Lyophilizer condenser was cooled to −75° C. and vacuum was maintained below 100 mTorr.
4. Frozen tubes were transferred into lyophilizer vacuum flask. Vacuum flask was attached to bulk lyophilizer port and immediately vacuum was applied.

5. Lyophilization was continued for about 72 hours.
6. After 72 hours vacuum was released and vacuum flask was removed from the lyophilizer.
7. Conical tubes containing lyophilized product were capped at an ambient condition and tapped on a hard surface to break the cake.

Injectability Evaluation:
1. Lyophilized product was filled into cyclic olefin copolymer (COC) PFS barrel or glass vial.
2. Required volume of water for injection was added.
3. Lyophilized product was reconstituted and injected into a foam (model: injectability with resistance) following directions for use (DFU) for Compound 1 injectable suspension.
4. Test parameters and observations were recorded in Table 7.

TABLE 7

Injectability Evaluation

| Container/ Closure | Mass (mg) | Reconstitution Volume (mL) | Observations |
| --- | --- | --- | --- |
| 5 mL COC PFS | 900 | 3.0 | Product was acceptably reconstituted within 10-20 sec shaking Rapid and continuous injection resulted in complete injection into a foam |
| 5 mL COC PFS | 900 | 3.0 | Product was acceptably reconstituted within 10-20 sec shaking Rapid and continuous injection resulted in complete injection into a foam |
| 5 mL COC PFS | 900 | 2.0 | Product was acceptably reconstituted within 10-20 sec shaking Slow injection resulted in needle clog into a foam Clog was removed and complete injection was performed rapidly into a foam |
| 5 mL COC PFS | 900 | 2.0 | Product was acceptably reconstituted within 10-20 sec shaking Rapid and continuous injection resulted in complete injection into a foam |
| 10 mL Glass Vials | 1400 | 2.5 | Product was acceptably reconstituted within 10-20 sec shaking Rapid and continuous injection resulted in complete injection into a foam |
| 10 mL Glass Vials | 1400 | 2.5 | Product was acceptably reconstituted within 10-20 sec shaking Rapid and continuous injection resulted in complete injection into a foam |
| 10 mL Glass Vials | 1400 | 2.5 | Product was acceptably reconstituted within 10-20 sec shaking Rapid and continuous injection resulted in complete injection into a foam |

Example V

Rapid Intramuscular (IM) Injection of Compound 1 on Pain and Injection Site Reactions (IRS)

Injection site reactions and pain upon IM injection of Compound 1 are a potential safety concern. A Phase 3, multicenter, extension study was conducted in 81 sites to assess the effect of rapid IM injections of Compound 1 on human patients diagnosed with stable schizophrenia. Briefly, 332 subjects enrolled in the study were assigned PFS. Compound 1 is formulated as a pre-filled syringe (PFS) of an extended release aqueous suspension of a therapeutically effective amount of Compound 1. An injection volume of 3.4 mL or 1.6 mL of the aqueous suspension was administered according to protocol I at a rate of less than 10 seconds by inserting the 20 gauge needle in the gluteal muscle. ISRs upon IM injection of Compound 1 were assessed at each visit. Over 5000 injections of Compound 1 have been administered intramuscularly with an ISR rate of less than 1%.

Protocol I

1. TAP the pre-filled syringe at least 10 times to dislodge any material that may have settled.
2. SHAKE the pre-filled syringe vigorously for a minimum of 30 seconds to ensure a uniform suspension.

If the syringe is not used within 15 minutes, re-suspend by shaking vigorously for 30 seconds.
3. SELECT the injection needle. For patients with a larger amount of subcutaneous tissue overlying the gluteal muscle, use the longer of the needles provided to ensure the injectate reaches the intramuscular mass. Both the 1½ and 2 inch administration needles are provided to accommodate varying patient body habitus.
4. ATTACH the injection needle. Remove the syringe tip cap with an easy counter-clockwise twisting motion. Attach the appropriate needle with an easy clockwise twisting motion. Remove the needle sheath with straight, firm pull.
5. PRIME the syringe to remove air. Bring the syringe into upright position and tap the syringe to bring air to the top. Remove air by depressing the plunger rod. A few drops of suspension will be released.
6. ADMINISTER the entire contents intramuscularly. Inject in a rapid and continuous manner (less than 10 seconds). DO NOT inject intravenously or subcutaneously.

Prior to injection aspirate for blood. [If blood aspirates, do not inject. Replace with new needle (Steps 3 & 4) and administer into an adjacent site in the same gluteal muscle (Steps 5 & 6).]

If you are unable to complete the injection, replace with new needle (Steps 3 & 4) and readminister into an adjacent site in the same gluteal muscle (Steps 5 & 6).
7. DISPOSE of the needle. Cover the needle by pressing the safety device. Dispose of used and unused items in a proper waste container.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The invention claimed is:

1. A method of treating schizophrenia in a subject in need thereof, comprising intramuscularly administering to said subject a therapeutically effective amount of a pharmaceutical composition at a continuous injection rate of 0.3 mL/s to 1 mL/s, wherein said pharmaceutical composition comprises:

(a) 24-30 weight percent of a compound of Formula (I):

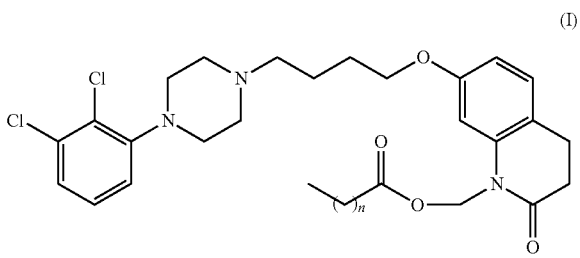

wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition;
wherein the pharmaceutical composition has a total injection volume from 1.0 mL to 10 mL; and
wherein the total pharmaceutical composition is continuously injected within 10 seconds at said rate.

2. The method of claim 1, wherein the said pharmaceutical composition comprises:
(a) about 26.6 weight percent Compound 1:

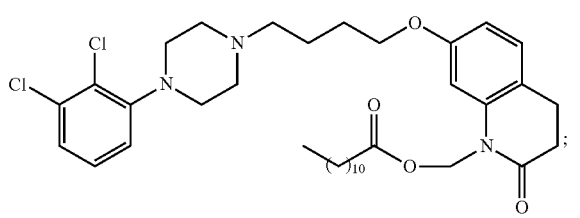

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

3. The method of claim 1, wherein the administration is instantaneous.

4. The method of claim 1, wherein the pharmaceutical composition is injected using a 20 to 23 gauge needle.

5. The method of claim 4, wherein the needle is a 20 gauge needle.

6. The method of claim 4, wherein the needle is a 21 gauge needle.

7. The method of claim 1, wherein the injection is administered to the subject in the dorsal gluteal muscle.

8. The method of claim 1, wherein the injection is administered to the subject in the deltoid muscle.

9. The method of claim 1, wherein the needle does not experience injection failure due to needle clogging.

10. The method of claim 1, wherein the method does not elicit a pain intensity above a normal threshold in the subject.

11. The method of claim 1, wherein the method does not elicit any injection site reactions in the subject above a normal threshold in the subject.

12. The method of claim 11, wherein the symptoms of the injection site reaction are selected from the group consisting of redness, tenderness, warmth, itching, pain at injection site, blistering, nodule formation, and severe skin damage.

13. The method of claim 1, wherein the total injection volume of the pharmaceutical composition is approximately 3.4 mL and the total pharmaceutical composition is injected within 10 seconds or wherein the total injection volume of the pharmaceutical composition is approximately 1.6 mL and the total pharmaceutical composition is injected within 5 seconds.

14. The method of claim 1, wherein the intramuscular injection rate is selected from the group consisting of: 0.4 mL/s, 0.5 mL/s, 0.6 mL/s, 0.7 mL/s, 0.8 mL/s, and 0.9 mL/s.

15. The method of any one of claims 1, 2, 3-9, 13, and 14, wherein the total injection volume of the pharmaceutical composition is from 1 mL to 4 mL.

16. A method of treating schizophrenia in a subject in need thereof, comprising intramuscularly injecting into said subject a therapeutically effective amount of a pharmaceutical composition, wherein said pharmaceutical composition comprises:
(a) 24-30 weight percent of a compound of Formula (I):

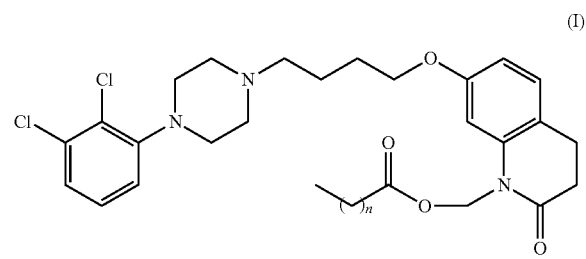

wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition; and
wherein the pharmaceutical composition has a total injection volume of approximately 3.4 mL, and the total pharmaceutical composition is continuously injected within 10 seconds at a rate of 0.3 mL/s to 1 mL/s.

17. The method of claim 16, wherein the said pharmaceutical composition comprises:
(a) about 26.6 weight percent Compound 1:

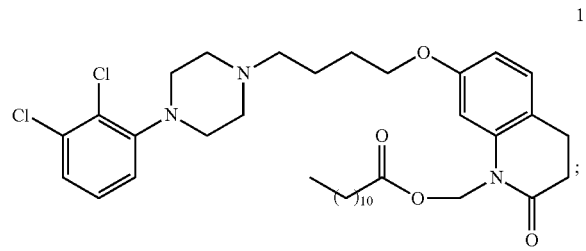

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

18. A method of treating schizophrenia in a subject in need thereof, comprising intramuscularly injecting into said subject a therapeutically effective amount of a pharmaceutical composition, wherein said pharmaceutical composition comprises:

(a) 24-30 weight percent of a compound of Formula (I):

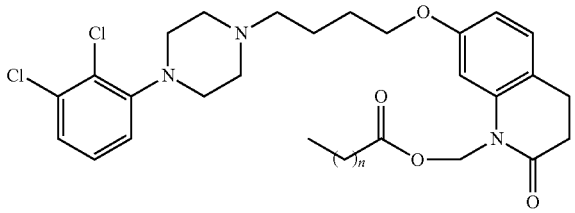

wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition; and
wherein the pharmaceutical composition has a total injection volume of approximately 1.6 mL, and the total pharmaceutical composition is continuously injected within 5 seconds at a rate of 0.3 mL/s to 1 mL/s.

19. The method of claim 18, wherein the said pharmaceutical composition comprises:

(a) about 26.6 weight percent Compound 1:

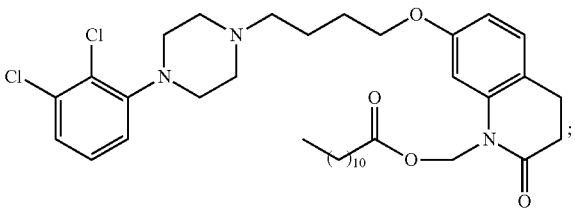

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

20. A method of treating schizophrenia in a subject in need thereof, comprising intramuscularly injecting into said subject a therapeutically effective amount of a pharmaceutical composition, wherein said pharmaceutical composition comprises:

(a) 24-30 weight percent of a compound of Formula (I):

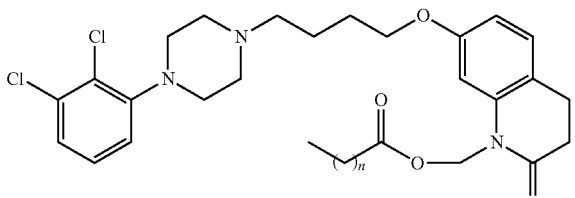

wherein n is an integer between 4 and 14;

(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition; and
wherein the pharmaceutical composition has a total injection volume of approximately 3.2 mL, and the total pharmaceutical composition is continuously injected within 10 seconds at a rate of 0.3 mL/s to 1 mL/s.

21. The method of claim 20, wherein the said pharmaceutical composition comprises:

(a) about 26.6 weight percent Compound 1:

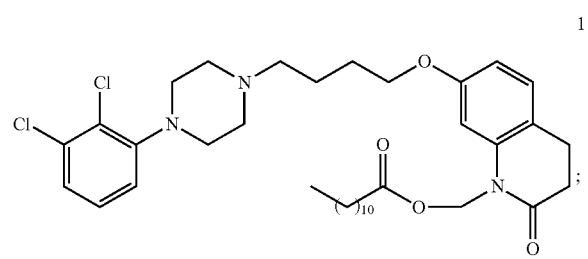

(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.

22. A method of treating schizophrenia in a subject in need thereof, comprising intramuscularly injecting into said subject a therapeutically effective amount of a pharmaceutical composition, wherein said pharmaceutical composition comprises:

(a) 24-30 weight percent of a compound of Formula (I):

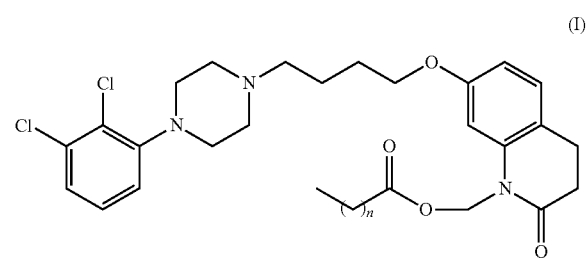

wherein n is an integer between 4 and 14;
(b) 0.3-0.4 weight percent sorbitan laurate;
(c) 0.1-0.3 weight percent polysorbate 20; and
(d) an aqueous vehicle
wherein the percentages of (a), (b), and (c) are relative to the total weight of the composition; and
wherein the pharmaceutical composition has a total injection volume of approximately 2.4 mL, and the total pharmaceutical composition is continuously injected within 8 seconds at a rate of 0.3 mL/s to 1 mL/s.

23. The method of claim 22, wherein the said pharmaceutical composition comprises:

(a) about 26.6 weight percent Compound 1:
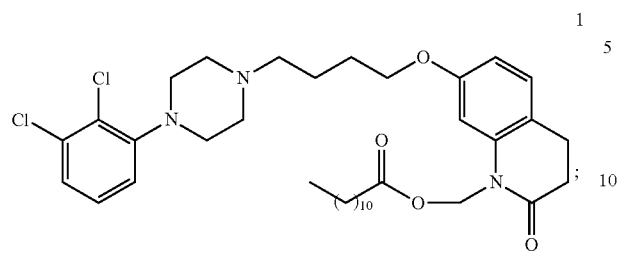
(b) about 0.37 weight percent sorbitan laurate;
(c) about 0.15 weight percent polysorbate 20; and
(d) an aqueous vehicle
wherein the percentages of (a), (b), and (c) are relative to the total weight of the composition.
24. The method of claim 1, wherein the composition has a total injection volume from 3 mL to 10 mL.
* * * * *